United States Patent [19]

Fleet et al.

[11] Patent Number: 5,013,842

[45] Date of Patent: May 7, 1991

[54] SYNTHESIS OF CHIRAL PYRROLIDINE AND PIPERIDINE GLYCOSIDASE INHIBITORS

[75] Inventors: George W. J. Fleet; David R. Witty, both of Oxford, United Kingdom

[73] Assignee: Monsanto Company, St. Louis, Mo.

[21] Appl. No.: 468,341

[22] Filed: Jan. 22, 1990

[51] Int. Cl.$^5$ .................. C07D 207/12; C07D 211/22
[52] U.S. Cl. .................................. 546/220; 546/242; 548/531; 548/532; 548/533; 548/556
[58] Field of Search ............... 546/242, 220; 548/556, 548/532, 531, 533

[56] References Cited

U.S. PATENT DOCUMENTS

| | | | |
|---|---|---|---|
| 4,469,875 | 9/1984 | Busker et al. | 548/532 |
| 4,611,058 | 9/1986 | Koebernick | 546/242 |
| 4,894,388 | 1/1990 | Fleet | 548/556 X |
| 4,937,357 | 6/1990 | Koszyk et al. | 548/556 |

OTHER PUBLICATIONS

Bashyal et al., Tetrahedron Letters, 27, pp. 3205–3208, (1986).
Austin et al., Tetrahedron, 43, pp. 3095–3108, (1987).
Bashyal et al., Tetrahedron, 43, pp. 423–430, (1987).
Bashyal et al., Tetrahedron, 43, pp. 415–422, (1987).
Tyms et al., Lancet, pp. 1025–1026 (1987).
Fleet et al., Febs Lett. 237, 128–132 (1988).
Fleet et al., Tetrahedron Lett. 26, 3127–3130 (1985).
Fleet and Smith, Tetrahedron 42, 5685–5692 (1986).
Fleet et al., Tetrahedron 43, 979–990 (1987).
Ziegler et al., Angew. Chem. Int. Ed. Engl. 27, 716 (1988).
von der Osten et al., J. Am. Chem. Soc. 111, 3924–3927 (1989).

*Primary Examiner*—Joseph Paul Brust
*Attorney, Agent, or Firm*—Scott J. Meyer; James W. Williams, Jr.

[57] ABSTRACT

There is disclosed a novel method for the syntheses of chiral pyrrolidines and piperidines by the intramolecular ring closure of anomeric mixtures of 4-amino- and 5-amino-2-trifluoromethanesulfonates of methyl furanosides. The novel method preferably provides for the efficient syntheses from diacetone glucose of 1,4-dideoxy-1,4-imino-D-arabinitol—known as DAB1, (2S,3R,4R)-3,4-dihydroxyproline, fagomine [1,5-imino-1,2,5-trideoxy-D-arabino-hexitol], and (2S,3R,4R)-3,4-dihydroxypipecolic acid by intramolecular nucleophilic displacement by an amino function of 2-O-trifluoromethanesulphonates of anomeric mixtures of methyl furanosides.

4 Claims, No Drawings

SYNTHESIS OF CHIRAL PYRROLIDINE AND PIPERIDINE GLYCOSIDASE INHIBITORS

BACKGROUND OF THE INVENTION

This invention relates to a method for the syntheses of chiral pyrrolidines and piperidines by the intramolecular ring closure of anomeric mixtures of 4-amino-and 5-amino-2-trifluoromethanesulfonates of methyl furanosides. More particularly, the invention relates to the efficient syntheses from diacetone glucose of 1,4-dideoxy-1,4-imino-D-arabinitol -known as DAB1- (1), (2S,3R,4R)-3,4-dihydroxyproline (2), fagomine [1,5-imino-1,2,5-trideoxy-D-arabino-hexitol](3), and (2S,3R,4R)-3,4-dihydroxypipecolic acid (4) by intramolecular nucleophilic displacement by an amino function of 2-O-trifluoromethanesulphonates of anomeric mixtures of methyl furanosides. All four of these compounds previously have been screened as potential inhibitors of HIV replication [Tyms et al., Lancet, pp. 1025-1026 (1987); Fleet et al., FEBS Lett. 237, 128-132 (1988)]as part of a project investigating the potential of amino sugar derivatives in dissecting glycoprotein biosynthesis. 1,4-dideoxy-1,4-imino-L-arabinitol, LAB1, the enantiomer of (1), is a powerful inhibitor of cytopathic effect of HIV at concentrations which were not cytotoxic.

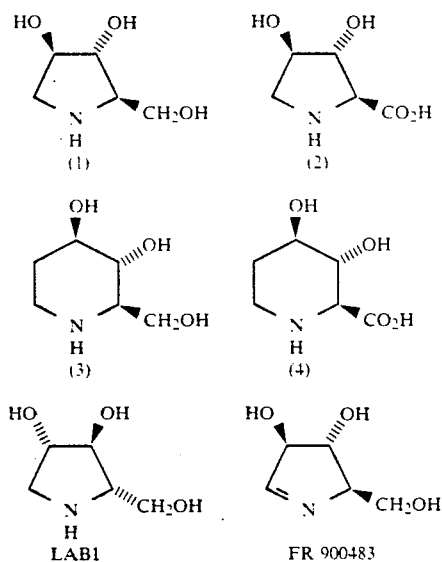

Naturally occurring and synthetic polyhydroxylated pyrrolidines and piperidines constitute a powerful class of glycosidase inhibitors. See, respectively, Fellows and Fleet, Alkaloidal Glycosidase Inhibitors from Plants, Chap. 13 in *Natural Product Isolation*, (ed. G. H. Wagman and R. Cooper), p. 540-560, Elsevier, (1988), and Fleet, Amino Sugar Derivatives and Related Compounds as Glycosidase Inhibitors *Topics in Medicinal Chemistry*, 4th *SCI-RSC Med. Chem. Symp. Cambridge*, Sept. 1987, (Ed. P. R. Leeming), p. 149-162, Royal Society of Chemistry, London, (1988). Both the natural product DAB1 (1), isolated from *Anglyocalyx boutiqueanus* [Nash et al., *Phytochemistry*, 24, 1620 (1985); Jones et al., *Tetrahedron Lett.* 26, 3127 (1985)]and *Arachniodes standishii*, [Furukawa et al., *Phytochemistry* 24, 593 (1985)]and its enantiomer LAB1 are powerful inhibitors of a range of α-glucosidases [Fleet et al., *Tetrahedron Lett.* 26, 3127 (1985); Scofield et al., *Life Sci.* 39, 645 (1986)].

DAB1 (1) has been synthesized previously from D-xylose [Fleet et al., *Tetrahedron Lett.* 26, 3127-3130 (1985); Fleet and Smith, *Tetrahedron* 42, 5685-5692 (1986)]and from (S)-glutamic acid [Ikota and Hanaki *Chem. Pharm. Bull.*, 35, 2140 (1987)]; LAB1has been prepared from D-xylose [Fleet et al., *Tetrahedron*, 42, 5685-5692 (1986); Naleway et al., *Carbohydr. Res.*, 179, 199 (1988)]and L-arabinose [Jones, supra.].

The structurally related fungal metabolite FR 900483, an anhydro form of 4-amino-4-deoxy-D-arabinose, has been shown to be an immunomodulator [Kayakira et al., *Tetrahedron Lett.* 29, 1725 (1988) and Shibata et al., *J. Antibiot.*, 41, 296 (1988)]; other hydroxylated pyrrolidines also may have promise as immunoregulator agents [Ikota and Hanaki, *Chem. Pharm. Bull.*, 36, 1143 (1988)].

Fagomine (3) isolated from *Fagopyrum esculentum* [Koyama and Sakamura, *Agric. Biol. Chem.*, 38, 1111 (1974); Koyama et al., *Agric. Biol. Chem.*, 38, 1467 (1974)]and as the 4-O-β-glucoside from *Xanthocercis zambesiaca* [Evans et al., *Tetrahedron Lett.*, 26, 1465 (1985)], is a moderate inhibitor of isomaltase [Scofield, supra.]. Fagomine has previously been prepared from glucose [Fleet et al., *Tetrahedron*, 43, 979-990 (1987)].

Both DAB1 (1) and fagomine have also been prepared by sequences involving aldolases [Ziegler et al., *Angew. Chem. Int. Ed. Engl.*, 27, 716 (1988); Pederson and Wong, *Heterocycles*, 28, 477 (1989); and von der Osten et al., *J. Am. Chem. Soc.* 111, 3924-3927 (1989)].

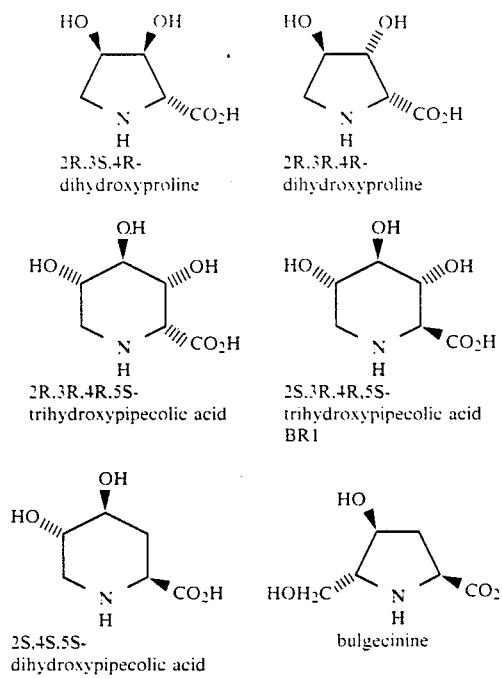

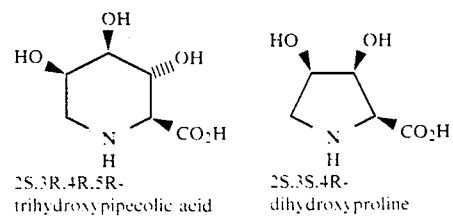

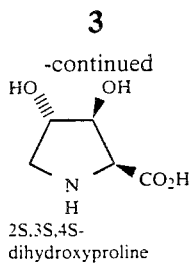

2S,3S,4S-dihydroxyproline

There is considerable interest in the synthesis of optically pure β- and γ-hydroxy-α-amino acids. Although a few good non-enzymic methods for their asymmetric synthesis have been devised [Jung and Jung, *Tetrahedron Lett.*, 30, 6637 (1989) and references cited therein], carbohydrates have long been established as homochiral starting meterials for the synthesis of non-protein amino acids [Hanessian, *Total Synthesis of Natural Products: The Chiron Approach*, Pergamon, Oxford, 1983; Shenbagamurthi et al., *J. Med. Chem.* 29, 802 (1986) and references cited therein]. The value of simply protected sugar lactones—in which azide is easily introduced at the carbon α to the lactone carbonyl—in short and efficient syntheses of highly functionalized amino acids such as hydroxylated prolines and pipecolic acids has been recognized. Thus, introduction of an azide function with retention of configuration at C-2 of D-ribonolactone [Dho et al., *Tetrahedron Lett.*, 27, 3203 to 3204 to 3208 (1986)] provides a powerful intermediate for the synthesis of homochiral D-amino acids such as 2R,3S,4R-dihydroxyproline [Baird et al., *J. Chem. Soc. Perkin Trans.* 1, 1785 (1987)]. Introduction of azide α to the carbonyl group of glucuronolactone [Bashyal et al., *Tetrahedron Lett.*, 27, 3205 (1986)] allowed short syntheses of the D-amino acids 2R,3R,4R-dihydroxyproline and 2R,3R,4R,5S-trihydroxypipecolic acids and of the L-amino acids 2S,3R,4R,5S-trihydroxypipecolic acid (BR1), 2S,4S,5S-dihydroxypipecolic acid and bulgecinine [Bashyal et al., *Tetrahedron* 43, 415–422 (1987); Bashyal et al., *Tetrahedron*, 43, 423 to 430 (1987)]. More lengthy syntheses derived by introduction of nitrogen at C-2 of glucose have been reported for the synthesis of 2S,3R,4R,5R-trihydroxypipecolic acid [Fleet et al., *Tetrahedron*, 43, 979–990 (1987)], BR1 [Bernotas and Ganem, *Tetrahedron Lett.*, 26 4981 (1985)] and bulgecinine [Wakamiya et al., *Tetrahedron Lett.*, 26 4759 (1985)]. 2S,3S,4R-Dihydroxyproline has been prepared by initial introduction of nitrogen at C-3 of glucose [Fleet et al., *Tetrahedron*, 43, 3095–3108 (1987)]; a similar approach has been used for the synthesis of other β-hydroxy-α-amino acids [Rao et al., *Tetrahedron Lett.*, 30, 6769 (1989)].

BRIEF DESCRIPTION OF THE INVENTION

In accordance with the present invention, a novel method for the syntheses of chiral pyrrolidines and piperidines by the intramolecular ring closure of anomeric mixtures of 4-amino- and 5-amino-2-trifluoromethanesulfonates of methyl furanosides is provided. The novel method preferably provides for the efficient syntheses from diacetone glucose of 1,4-dideoxy-1,4-imino-D-arabinitol—known as DAB1—(1), (2S,3R,4R)-3,4-dihydroxyproline (2), fagomine [1,5-imino-1,2,5-trideoxy-D-arabino-hexitol] (3), and (2S,3R,4R)-3,4-dihydroxypipecolic acid (4) by intramolecular nucleophilic displacement by an amino function of 2-O-trifluoromethanesulphonates of anomeric mixtures of methyl furanosides.

In accordance with the invention a protected xylose, namely 3-O-benzyl-1,2-O-isopropylidene-α-D-xylofuranose (8), which is readily prepared from diacetone glucose, is used as a divergent intermediate for the efficient syntheses of DAB1 (1), (2S,3R,4R)-3,4-dihydroxyproline (2), fagomine (3) and (2S,3R,4R)-3,4-dihydroxypipecolic acid (4). Syntheses of these compounds is preferably carried out by the stepwise method as follows in which combound numbers in parentheses correspond to compounds shown by chemical structure herein:

Syntheses of DAB1 and (2S,3R,4R)-3,4-Dihydroxyproline (a) 3-O-Benzyl-1,2-O-isopropylidene-α-D-xylofuranose (8) is esterified at the primary hydroxyl with methanesulfonyl chloride to give the corresponding mesylate (9), (b) The mesylate (9) is reacted with azide ion, e.g. sodium azide, to introduce the azide function at C-5 and give the furanose (10), (c) The furanose (10) is converted to the methyl furanosides (11) as a mixture of the α and β anomers by treatment with methanolic hydrogen chloride, (d) The methyl furanosides (11) are esterified at the free hydroxyl at C-2 with triflic anhydride to give the corresponding triflates (12), (e) The triflates (12) are catalytically hydrogenated, e.g. in the presence of palladium on carbon, to reduce the azide to the corresponding amine and provide ring closure to give the iminolyxofuranosides (13), (f) The iminolyxofuranosides (13) are converted to the carbamates (14) by reaction with benzyl chloroformate.

(g) The carbamates (14) are subjected to acid hydrolysis to give the lactol or protected iminolyxose (15).

(h) The lactol (15) is (i) reduced with sodium borohydride to give diol (16) from which the protecting groups are removed by hydrogenolysis to give the desired DAB1 (1) or (ii) oxidized with bromine to give the benzyl-protected proline derivative (17) which is subject to hydrogenolytic removal of the protecting group to give the desired (2S,3R,4R)-dihydroxyproline (2).

Syntheses of Fagomine and (2S,3R,4R)-3,4-Dihydroxypipecolic acid (a) 3-O-Benzyl-1,2-O-isopropylidene-α-D-xylofuranose (8) is esterified at the free hydroxyl with triflic anhydride to give the triflate (18), (b) The triflate (18) is reacted with alkali metal cyanide to give the nitrile (19), (c) The nitrile (19) is converted to the methyl furanosides (20) as a mixture of the α and β anomers by treatment with methanolic hydrogen chloride, (d) The methyl furanosides (20) are converted to the triflates (21) by reaction with triflic anhydride, (e) The triflates (21) are reduced with borane-dimethyl sulfide to the corresponding 6-amino sugar which after treatment with alkali metal carbonate gives the bicyclic amines (22), (f) The bicyclic amines (22) are converted to the carbamates (23) by reaction with benzyl chloroformate, (g) The carbamates (23) are subjected to acid hydrolyses to give the lactol (24), (h) The lactol (24) is (i) reduced with sodium borohydride to give diol (25) from which the protecting groups are removed by hydrogenolyis to give the desired fagomine (3) or (ii) oxidized with bromine to give the benzyl-protected pipecolic derivative (26) which is subjected to hydrogenolytic removal of the protecting groups to give the desired (2S,3R,4R)-3,4-dihydroxypipecolic acid (4).

Other such suitable reactants for use in the foregoing syntheses of DAB1, (2S,3R,4R)-3,4-dihydroxyproline, fagomine and (2S,3R,4R)-3,4-dihydroxypipecolic acid will be apparent to the person skilled in the art after reading the present disclosure. These reactants are generally used in proportions such as to satisfy the stoichiometry of the above reaction steps. Illustrative of suitable reactants are the use of a noble metal catalyst such as platinum or palladium on carbon for the catalytic hydrogenation; use of sodium azide, potassium azide or tetrabutylammonium azide to introduce the azide function; use of sodium cyanide or potassium cyanide to form the nitrile; use of hydroxyl protecting groups such as isopropylidene or cyclohexylidene; use of sodium borohydride, potassium borohydride or borane-dimethyl sulfide as reducing agents; use of trifluoroacetic acid for the hydrolytic removal of protecting groups; and use of organic solvents such as dioxane, DMF, THF, DMSO, N-methylpyrrolidine, pyridine, acetonitrile and the like as solvent media for the reaction steps.

The invention thus provides a new method for the synthesis of polyfunctionalized amino acids in which the nitrogen is first introduced in the sugar at C-5 [for a pyrrolidine—(2S,3R,4R)-3,4-dihydroxyproline (2)] and at C-6 [for a piperidine—(2S,3R,4R)-3,4-dihydroxypipecolic acid (4)]. Both racemic and optically active (2) have previously been synthesized from racemic and resolved 3,4-dehydroproline. See, respectively, Hudson et al., *Aust. J. Chem.*, 28, 2479 (1975), and Kahl and Wieland, *Leibigs Ann. Chem.*,, 1445 (1981). Homochiral (2), together with 2S,3S,4S-dihydroxyproline [the enantiomer of the dihydroxyproline obtained from glucuronolactone], has been prepared from β-hydroxyallyl glycine derivatives [Ohfune and Kurokawa, *Tetrahedron Lett.*, 26 5307 (1985)]. Synthesis of (2S,3R,4R)-3,4-Dihydroxy-pipecolic acid (4) has not previously been reported, although its structure is disclosed by Fleet et al., *FEBS Lett.* 237, 128–132 (1988).

bicyclic intermediates, such as (13), formed from the ring closure from a nitrogen function at C-2 of a furanoside onto a leaving group at C-5 of a sugar have been used in the synthesis of the homochiral pyrrolidines 2R,5R-dihydroxymethyl-3R,4R-dihydroxypyrrolidine [Fleet and Smith, *Tetrahedron Lett.*, 26, 1469 (1985); Fleet and Smith, *Tetrahedron*, 43, 971–978 (1987)], the pyrrolizidine alkaloid alexine and some of its diastereomers [Fleet et al., *Tetrahedron Lett.*, 29, 5441–5444 (1988)] and DAB1 (1) [Fleet and Smith, *Tetrahedron*, 42, 5685–5692 (1986)]. The major practical problems in those syntheses is the introduction of nitrogen by nucleophilic substitution by azide ion of a triflate at C-2 of a furanoside. While 2-O-trifluoromethane-sulphonates of furanosides in which the triflate leaving group is cis to the anomeric substituent undergo sufficient nucleophilic displacement by azide, triflates which are trans to the anomeric substituent give low yields of $S_N2$ products; thus, such syntheses require a wasteful—and frequently experimentally tricky—separation of the furanoside anomers. The present invention demonstrates that intramolecular displacement of a triflate at C-2 of a furanoside by a 5-amino group to give such bicyclic pyrrolidines occurs easily with both α- and β-anomers.

DETAILED DESCRIPTION OF THE INVENTION

The invention is conveniently illustrated by the following description of preferred embodiments in which compound numbers in parentheses correspond to compounds shown by chemical structure herein.

The synthesis of DAB1 (1) and the dihydroxyproline (2) requires introduction of nitrogen at C-5 of a suitably protected derivative of xylose. Diacetone glucose was converted to the protected xylofuranose (8) by minor changes to literature procedures [Anderson and Nabinger, *Tetrahedron Lett.*, 24, 2743 (1983)]. Thus, reaction of diacetone glucose (5) with sodium hydride and benzyl bromide in tetrahydrofuran in the presence of tetrabutyl ammonium iodide gave the fully protected furanose (6) [97% yield] [Iwashigi and Saeki, *Chem. Pharm. Bull.*, 15, 1803 (1967)] which on hydrolysis by acetic acid in aqueous methanol afforded the diol (7) [87% yield] [Meyer and Reichstein, *Helv. Chim. Acta*, 29, 152 (1946)]. Periodate oxidation of the diol (7), followed by treatment with sodium borohydride in aqueous ethanol gave the divergent intermediate, 3-O-benzyl-1,2-O-isopropylidene-α-D-xylofuranose (8) [Nakagawa et al., *Bull. Chem. Soc. Jpn.*, 40, 2150 (1967)], in 88% yield [74% overall yield from (5)].

Esterification of the primary hydroxyl function in (8) with methanesulphonyl chloride in pyridine gave the corresponding mesylate (9) [94% yield] which with sodium azide in dimethyl formamide introduced the azide function at C-5 of the sugar to give (10) [97% yield]. Treatment of the furanose (10) with methanolic hydrogen chloride gave the methyl furanosides (11) [82% yield] as an anomeric mixture in which the β-isomer was in marginal excess.

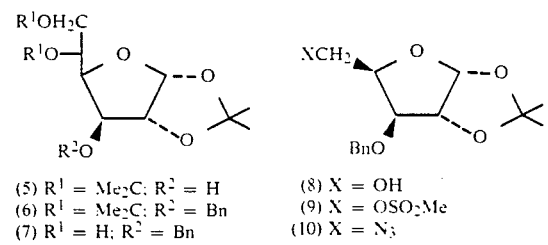

(5) $R^1 = Me_2C; R^2 = H$
(6) $R^1 = Me_2C; R^2 = Bn$
(7) $R^1 = H; R^2 = Bn$ (8) X = OH
(9) X = $OSO_2Me$
(10) X = $N_3$

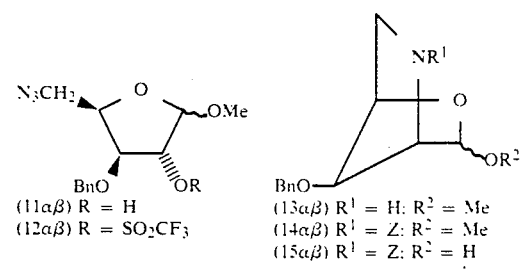

(11α,β) R = H
(12α,β) R = $SO_2CF_3$ (13α,β) $R^1 = H; R^2 = Me$
(14α,β) $R^1 = Z; R^2 = Me$
(15α,β) $R^1 = Z; R^2 = H$

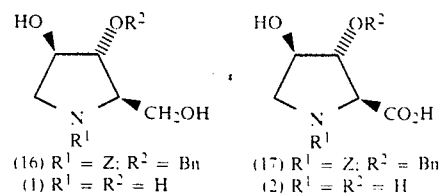

(16) $R^1 = Z; R^2 = Bn$
(1) $R^1 = R^2 = H$

(17) $R^1 = Z; R^2 = Bn$
(2) $R^1 = R^2 = H$

Although the anomers of (11) are easily separable, the subsequent reactions may be carried out on a mixture of anomers with no reduction in the yield of cyclized products obtained. The remaining free hydroxyl group at C-2 in (11) was reacted with trifluoromethanesulphonic anhydride in dichloromethane in the presence of pyridine to give the corresponding triflates (12) in 92% yield for the α-anomer and in 78% yield for the β-anomer. Hydrogenation of (12α) in ethyl acetate in the presence of 5% palladium on charcoal caused reduction of the azide to the corresponding amine which underwent spontaneous cyclization to give the iminolyxofuranoside (13α) in 95% yield; similar treatment of (12β) gave (13β) in 93% yield. The bicyclic amines (13αβ) are relatively unstable compounds and were immediately converted to the carbamates (14αβ) by reaction with benzyl chloroformate in a biphasic mixture of ether and saturated sodium bicarbonate in 76% yield for the α-anomer and in 90% yield for the β-anomer. Hydrolysis of (14α) with aqueous trifluoroacetic acid gave the protected iminolyxose (15) in 92% yield; similar hydrolysis of the β anomer gave (15) in 87% yield. Reduction of the lactol (15) with sodium borohydride in aqueous ethanol gave (16) in 98% yield. Removal of the carbamate and O-benzyl protecting groups in (16) by hydrogenolysis in acetic acid in the presence of palladium black gave DAB1 (1) in 98% yield, isolated as the easily crystallized hydrochloride. The overall yield of DAB1 (1) was 44% from the divergent intermediate or protected xylose (8) and 33% from diacetone glucose (5). Oxidation of the lactol (15) with bromine in aqueous dioxane containing barium carbonate gave the Z-protected (benzyloxy) proline derivative (17) [75% yield] from which the free amino acid (2) was obtained by hydrogenolytic removal of the protecting groups [palladium black, acetic acid] in 94% yield. The overall yield of (2S,3R,4R)-3,4-dihydroxy proline (2) was 24% from the divergent intermediate or protected xylose (8) and 18% from diacetone glucose (5).

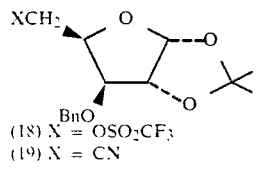
(18) X = OSO₂CF₃
(19) X = CN

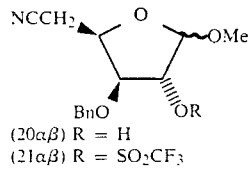
(20αβ) R = H
(21αβ) R = SO₂CF₃

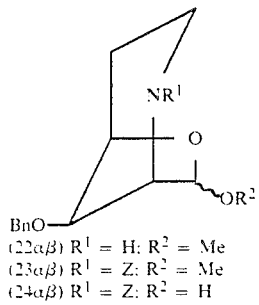
(22αβ) R¹ = H; R² = Me
(23αβ) R¹ = Z; R² = Me
(24αβ) R¹ = Z; R² = H

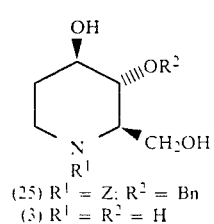
(25) R¹ = Z; R² = Bn
(3) R¹ = R² = H

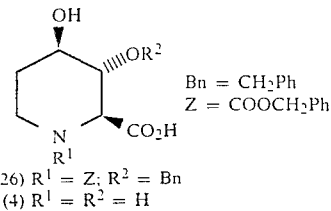
(26) R¹ = Z; R² = Bn
(4) R¹ = R² = H

Bn = CH₂Ph
Z = COOCH₂Ph

For the synthesis of fagomine (3) and dihydroxypipecolic acid (4), the free hydroxyl group in (8) was esterified with trifluoromethanesulphonic anhydride in the presence of pyridine to give the triflate (18) [94% yield] which, with potassium cyanide in dimethyl formamide, afforded the nitrile (19) [97% yield]; this excellent yield in the displacement of the triflate ester (8) is in marked contrast to the reaction of cyanide with the corresponding mesylate (9) which gave a very low yield of displacement product. Treatment of the cyanide (19) with methanolic hydrogen chloride gave the methyl furanosides (20) in a yield of 95% as a mixture of anomers in an α:β ratio of 3:4. The mixture of anomers (20) was converted to the corresponding triflates (21) [95% yield]; reduction of the nitriles (21) with borane-dimethyl sulphide to the corresponding 6-amino sugar gave, after work up with potassium carbonate, the bicyclic piperidines (22) in 96% yield. This excellent yield for the cyclization of a mixture of anomers confirms the value of this method for the synthesis of chiral piperidines, which is analogous to strategy used for efficient synthesis of deoxymannojirimycin [Fleet et al., *Tetrahedron*, 45, 327–336 (1989)]. The bicyclic amines (22) were reacted with benzyl chloroformate and the resulting carbamates (23) hydrolyzed by aqueous trifluoroacetic acid to afford the lactols (24) in an overall yield of 77%. Reduction of the lactols (24) by sodium borohydride in aqueous ethanol gave (25) in 97% yield; hydrogenolytic removal of the protecting groups gave fagomine (3), (98% yield), again isolated as the easily crystallized hydrochloride. The overall yield of fagomine (3) was 45% from the divergent intermediate or protected xylose (8) and 34% from diacetone glucose (5). Oxidation of the lactol (24) with bromine in aqueous dioxane containing barium carbonate gave the Z-protected (benzyloxy) pipecolic acid derivative (26) [84% yield] from which the free amino acid (4) was obtained as the monohydrate by hydrogenolytic removal of the protecting groups in 89% yield. The overall yield of (2S,3R,4R)-3,4-dihydroxy pipecolic acid (4) was 34% from the divergent intermediate or protected xylose (8) and 25% from diacetone glucose (5).

The following examples will further illustrate the present invention although it will be appreciated that the invention is not limited to these specific examples. M.p.s were recorded on a Kofler block. Infra red spectra were recorded on Perkin Elmer 297 or 781 spectrophotometers; unless otherwise stated, infra red spectra of solids were obtained in CHCl₃ solution and those of syrups as thin films. ¹H NMR spectra were run at 200 MHz on a Varian Gemini 200, or at 300 MHz on a Bruker WH 300 spectrometer; ¹³C NMR were recorded on Varian Gemini 200 (50.3 MHz) or Bruker AM 250 (62.9 MHz) spectrometers. All NMR spectra were obtained using deuteriochloroform as solvent unless otherwise stated; for ¹³C NMR spectra in D₂O, 1,4-dioxan (67.6) was used as an internal standard. Mass spectra were recorded on VG Micromass 16F or 30F spectrometers, using the desorption chemical ionisation technique (DCI NH$_3$) unless otherwise stated. Optical rotations were measured on a Perkin Elmer 241 polarimeter; concentrations are given in g/100 ml. Microanalyses were performed by the microanalytical service of the Dyson Perrins laboratory. TLC was performed on glass plates coated with silica gel blend 41 or on aluminium sheets pre-coated with Merck silica gel 60F$_{254}$, and compounds were visualised with sprays of 5% v/v concentrated sulphuric acid in methanol, 5% w/v ninhydrin in ethanol or a solution of 0.2% w/v ceric sulphate and 5% ammonium molybdate in 2M sulphuric acid. Flash chromatography was carried out using Merck Kieselgel 60, 230-400 mesh, and dry column chromatography using Merck Kieselguhr 60H. The solvent system CMAW refers to a mixture of chloroform, methanol, acetic acid and water in ratio 60:30:3:5. The following ion exchange resins were utilised: Aldrich Chemical Company 50x 8-100, Sigma OG 120 (fine mesh) Na$^+$ form, Sigma OG 400 Cl$^-$ form. The acid resin was used in the H$^+$ form, eluting with 0.5M NH$_3$ solution in the cases of amino alcohols and 0.5M pyridine solution for amino acids. The basic resin was used as the OH$^-$ form, with water as eluent and used only for purification of amino alcohols. Solutions in organic solvents were dried with anhydrous sodium sulphate unless stated otherwise, and solvents were removed under reduced pressure.

EXAMPLE 1

3-O-Benzyl-1,2:5,6-di-O-isopropylidene-α-D-glucofuranose (6)

A solution of diacetone glucose (5) (Aldrich) (18.0 g, 69.1 mmol) in THF (80 ml) was added dropwise to a stirred suspension of sodium hydride, (50% dispersion in oil, 3.67 g, 76.5 mmol) and tetrabutylammonium iodide (0.2 g, 0.54 mmol) in THF (50 ml) at 0° C. The mixture was warmed to room temperature and benzyl bromide (9.04 ml, 13.0 g, 76.0 mmol) added, then heated to 50° C. for 2 hours. Methanol (20 ml) was added and the mixture stirred for a further 2 hours before cooling, filtering through celite and concentrating. The resulting oil was dissolved in dichloromethane (100 ml), washed with water (2×30 ml), dried, filtered and evaporated to give 3-O-benzyl-1,2:5,6-di-O-isopropylidene-α-D-glucofuranose (23.5 g, 97%) as a pale brown oil. A small quantity was purified by flash chromatography (ethyl acetate-hexane 1:5) to give a clear oil, $[\alpha]_{20}^D$ −29.8° (c, 1.06 in chloroform) [lit.[43] −27.7° (c, 3.32 in ethanol)]; $^1$H NMR δ 1.32, 1.39, 1.44, 1.51 (12H, 4×s, 2×acetonide); 3.99-4.11 (5H, m, H-3, H-4, H-5, H-6,6'); 4.59 (1H, d, H-2); 4.59 (1H, d, H-2); 4.65, 4.70 (2H, 2×d, CH$_2$Ph, J$_{H,H'}$ 11.8 Hz); 5.90 (1H, d, H-1, J$_{1,2}$ 3.7 Hz); 7.32-7.36 (5H, m, H-Ph).

EXAMPLE 2

3-O-Benzyl-1,2-O-isopropylidene-α-D-glucofuranose (7)

Crude 3-O-benzyl-1,2:5,6-di-O-isopropylidene-α-D-glucofuranose (6) (23.5 g, 75.6 mmol) was dissolved in a 1:1:1 mixture of methanol, acetic acid and water (200 ml) and stood at 50° C. for 16 hours. The solvents were evaporated and the crude syrup purified by flash chromatography (ethyl acetate-hexane 3:2) to give 3-O-benzyl-1,2-O-isopropylidene-α-D-glucofuranose (18.1 g, 87%) as a clear oil, $[\alpha]_{20}^D$ −49.9° (c, 1.08 in chloroform) [lit.[44] −50.8° (c, 1.24 in chloroform)]; $^1$H NMR δ 1.33, 1.49 (6H, 2×s, acetonide); 2.17 (2H, bs, 2×OH); 3.69, 3.81 (2H, 2×dd, H-6,6', J$_{6,6'}$ 11.4 Hz, J$_{5,6}$ 5.5 Hz, J$_{5,6'}$ 3.4 Hz); 4.00-4.15 (3H, m, H-3, H-4, H-5); 4.56, 4.73 (2H, 2×d, CH$_2$Ph, J$_{H,H'}$ 11.7 Hz); 4.63 (1H, d, H-2); 5.94 (1H, d, 1-H, J$_{1,2}$ 3.7 Hz); 7.31-7.38 (5H, m, H-Ph).

EXAMPLE 3

3-O-Benzyl-1,2-O-isopropylidene-α-D-xylofuranose (8)

Sodium periodate (17.3 g, 81.1 mmol) was added portionwise to a stirred solution of 3-O-benzyl-1,2-O-isopropylidene-α-D-glucofuranose (7) (17.3 g, 55.8 mmol) in 10% aqueous ethanol (400 ml). After 3 hours, dichloromethane (100 ml) was added and the precipitate filtered off, washing the residue with dichloromethane. The combined organic layers were concentrated to 350 ml and cooled to 0° C. Sodium borohydride (4.09 g, 181 mmol) dissolved in 20% aqueous ethanol (150 ml) was added dropwise over 10 minutes, then the solution was stirred for 8 hours at room temperature. Excess ammonium chloride was added and the solution concentrated by evaporation. 10% sodium thiosulphate solution (200 ml) was added and the product extracted into dichloromethane (4×100 ml), dried, filtered and evaporated to give 3-O-benzyl-1,2-O-isopropylidene-α-D-xylofuranose (13.8 g, 88%) as a clear oil.[45] A small quantity was purified by flash chromatography (ether-hexane 2:1), $[\alpha]_{20}^D$ −69.1° (c, 1.07 in chloroform); $^1$H NMR δ 1.33, 1.49 (6H, 2×s, acetonide); 2.20 (1H, bs, OH); 3.86, 3.95 (2H, 2×dd, H-5,5', J$_{5,5'}$ 12.0 Hz, J$_{4,5}$ 4.8 Hz, J$_{4,5'}$ 5.2 Hz); 4.02 (1H, d, H-3, J$_{3,4}$ 3.5 Hz); 4.29 (1H, m, H-4); 4.50, 4.72 (2H, 2×d, CH$_2$Ph, J$_{H,H'}$ 12.0 Hz); 4.65 (1H, d, H-2); 5.99 (1H, d, H-1, J$_{1,2}$ 3.8 Hz); 7.31-7.38 (5H, m, H-Ph).

EXAMPLE 4

3-O-Benzyl-1,2-O-isopropylidene-5-O-methanesulphonyl-α-D-xylo-furanose (9)

A solution of 3-O-benzyl-1,2-O-isopropylidene-α-D-xylofuranose (8) (5.00 g, 17.9 mmol) in pyridine (30 ml) was cooled to 0° C. under nitrogen. Methanesulphonyl chloride (2.76 ml, 35.7 mmol, 2.0 molar equivalents) was added with stirring and the solution allowed to warm to room temperature over two hours. The reaction mixture was poured into brine (100 ml), extracted into dichloromethane (4×50 ml) and the combined organic phase dried, filtered, and evaporated. Purification by flash chromatography (ether-hexane 1:1) afforded 3-O-benzyl-1,2-O-isopropylidene-5-O-methanesulphonyl-α-D-xylo-furanose (6.01 g, 94%), m.p. 61°-62° C., $[\alpha]_{20}^D$ +113.5° (c, 0.96 in chloroform); ν$_{max}$ (chloroform) 2920, 1360, 1175, 1080 and 910 cm$^{-1}$; $^1$H NMR δ 1.33, 1.50 (6H, 2×s, acetonide); 3.02 (3H, s, CH$_3$); 4.01 (1H, d, 3-H, J$_{3,4}$ 2.8 Hz); 4.01-4.50 (4H, m, H-4, H-5,5', CHPh); 4.65 (1H, d, H-2, J$_{1,2}$ 3.8 Hz); 4.69 (1H, d, CH'Ph, J$_{H,H'}$ 11.8 Hz); 5.97 (1H, d, H-1); 7.31-7.38 (5H, m, H-Ph). $^{13}$C NMR δ 26.30, 26.85 (2×q, CH$_3$-acetonide); 37.56 (q, CH$_3$S); 67.59 (t, C-5); 72.12 (t, CH$_2$Ph); 77.98, 81.61, 82.08 (3×d, C-2,3,4); 105.35 (d, C-1); 112.19 (s, acetonide); 127.84, 128.24, 128.64 (3×d, HC-Ph); 136.91 (s, C-Ph). m/z: 376 (M+NH$_4^+$, 100%), 318 (32%). (Found C, 53.62; H, 6.19. C$_{16}$H$_{22}$SO$_6$ requires C, 54.03; H, 6.19).

EXAMPLE 5

5-Azido-3-O-benzyl-5-deoxy-1,2-O-isopropylidene-α-D-xylofuranose (10)

Sodium azide (2.72 g, 41.9 mmol) was added to a stirred solution of 3-O-benzyl-1,2-O-isopropylidene-5-O-methanesulphonyl-α-D-xylo-furanose (9) (5.00 g, 14.0 mmol) in dry DMF (100 ml) and the mixture kept at 70° C. for 12 h. The solvent was removed, the resulting oil poured into brine (50 ml), and the product extracted into dichloromethane (3 × 50 ml). The combined organic phase was dried, filtered and evaporated. Purification by flash chromatography (ether-hexane 1:2) gave 5-azido-3-O-benzyl-5-deoxy-1,2-O-isopropylidene-α-D-xylofuranose (4.11 g, 97%) as a clear oil, $[\alpha]_{20}^D$ −27.5° (c, 1.00 in chloroform); $\nu_{max}$ (film) 2920, 2000 ($N_3$), 1455 and 1075 cm$^{-1}$; $^1$H NMR δ 1.34, 1.51 (6H, 2×s, acetonide); 3.48, 3.60 (2H, 2×dd, H-5,5', $J_{5,5'}$ 12.5 Hz); 3.96 (1H, d, H-3); 4.32 (1H, dt, H-4, $J_{4,5}$ 6.5 Hz, $J_{4,5'}$ 6.8 Hz, $J_{3,4}$ 3.3 Hz); 4.65 (1H, d, H-2, $J_{2,3}$ 3.8 Hz); 4.53, 4.70 (2H, 2×d, CH$_2$, $J_{H,H'}$ 11.8 Hz); 5.95 (1H, d, H-1, $J_{1,2}$ 3.8 Hz); 7.32–7.38 (5H, m, H-Ph). $^{13}$C NMR δ 26.13, 26.68 (2q, acetonide); 111.76 (s, acetonide); 49.12 (t, C-5); 71.77 (t, CH$_2$Ph); 78.66, 81.45, 81.97 (3d, C-2, C-3, C-4); 104.99 (d, C-1); 127.64, 127.96, 128.42 (3d, HC-Ph); 137.04 (s, C-Ph). m/z (CI NH$_3$): 323 (M+NH$_4^+$, 20%), 278 (100%), 220 (32%), 91 (40%). (Found C, 58.86; H, 6.37; N, 13.46. $C_{15}H_{19}N_3O_4$ requires C, 59.01; H, 6.27; N, 13.76).

EXAMPLE 6

Methyl 5-Azido-3-O-benzyl-5-deoxy-D-xylofuranoside (11αβ)

5-azido-3-O-benzyl-5-deoxy-D-1,2-O-isopropylidene-α-D-xylofuranoside (10) (3.85 g, 12.6 mmol) was added to a solution of acetyl chloride (5.89 g, 0.075 mol) in methanol (75 ml) and stood at 0° C. under nitrogen for 36 hours. The solution was neutralised with excess anhydrous sodium bicarbonate and, after the addition of dichloromethane (100 ml), filtered and concentrated. Purification by flash chromatography (ether-hexane 2:1) gave the separate and anomers of methyl-5-azido-3-O-benzyl-5-deoxy-D-xylofuranoside as colourless oils.

α-anomer (1.35 g, 38%), $R_f$ 0.45 (ether-hexane 3:1); $[\alpha]_{20}^D$ +99.6° (c, 1.14 in chloroform); $\nu_{max}$ (film) 3470 (OH), 2930, 2095 ($N_3$), 1450, 1120 and 1040 cm$^{-1}$; $^1$H NMR δ 1.65 (1H, bs, OH); 3.45–3.51 (2H, m, H-5); 3.50 (3H, s, CH$_3$); 4.01 (1H, dd, H-3); 4.29 (1H, dd, H-2, $J_{2,3}$ 4.1Hz); 4.33 (1H, dd, H-4 $J_{3,4}$ 6.1Hz); 4.58, 4.79 (2H, 2×d, CH$_2$Ph, $J_{H,H'}$ 12 Hz); 5.00 (1H, d, H-1, $J_{1,2}$ 4.7 Hz); 7.30–7.37 (5H, m, H-Ph). $^{13}$C NMR δ 50.73 (t, C-5); 55.70 (q, CH$_3$); 71.77 (t, CH$_2$Ph); 76.99 (2d, C-3, C-4); 83.2 (d, C-2); 101.76 (d, C-1); 127.67, 127.81, 128.40 (3×d, HC-Ph); 137.61 (s, C-Ph). m/z: 252 (100%), 91 (53%), 220 (30%), 297 (M+NH$_4^+$, 30%). (Found C, 55.66; H, 6.31; N, 14.79. $C_{13}H_{17}N_3O_4$ requires C, 55.91; H, 6.14; N, 15.04).

β-anomer (1.53 g, 44%), $R_f$ 0.40 (ether-hexane 3:1); $[\alpha]_{20}^D$ −30.5° (c, 1.11 in chloroform); $\nu_{max}$ (film) 3420 (OH), 2920, 2100 ($N_3$), 1450, 1110 and 1050 cm$^{-1}$; $^1$H NMR δ 1.65 (1H, bs, OH); 3.39, 3.56 (2H, 2×dd, H-5,5', $J_{5,5'}$ 13.0 Hz); 3.45 (3H, s, CH$_3$); 4.02 (1H, dd, H-3); 4.28 (1H, dd, H-2 $J_{2,3}$ 3.4 Hz); 4.40 (1H, ddd, H-4, $J_{3,4}$ 6.5 Hz, $J_{4,5}$ 4.4 Hz, $J_{4,5'}$ 13.02 Hz); 4.58, 4.70 (2H, 2×d, CH$_2$Ph, $J_{H,H'}$ 12.1 Hz); 4.83 (1H, d, H-1, $J_{1,2}$ 1.1 Hz); 7.29–7.39 (5H, m, H-Ph). $^{13}$C NMR δ 51.94 (t, 5-C); 55.77 (q, CH$_3$); 72.47 (t, CH$_2$Ph); 79.74, 79.59 (2d, C-3, C-4); 83.42 (d, C-2); 109.61 (d, C-1); 127.76, 127.99, 128.49, (3×d, HC-Ph); 137.42 (s, C-Ph). m/z (NH$_3$ CI): 297 (M+NH$_4^+$, 30%), 252 (100%), 220 (90%), 91 (95%). (Found C, 55.69; H, 6.28; N, 14.65. $C_{13}H_{16}N_3O_4$ requires C, 55.91; H, 6.14; N, 15.04).

EXAMPLE 7

Methyl 5-Azido-3-O-benzyl-5-deoxy-2-O-trifluoromethanesulphonyl-D-xylofuranoside (12αβ)

A solution of methyl 5-azido-3-O-benzyl-5-deoxy-α-D-xylofuranoside (11) (1.18 g, 4.43 mmol) in dichloromethane (50 ml) was cooled, under nitrogen, to −50° C. Dry pyridine (820 l 10.2 mmol) and trifluoromethanesulphonic anhydride (853 l, 5.07 mmol) were added sequentially to the stirred solution, which was allowed to warm to −30° C. over 1 hour. Excess anhydride was quenched with methanol (0.5 ml) and the solution warmed to room temperature then poured into brine (50 ml). The aqueous layer was separated and extracted with dichloromethane (3×50 ml). The combined organic phase was dried and concentrated to give a yellow oil which on purification by flash chromatography (10% ether in hexane) afforded methyl 5-azido-3-O-benzyl-5-deoxy-2-O-trifluoromethanesulphonyl-α-D-xylofuranoside (1.60 g, 92%) as a clear oil, $R_f$ 0.65 (ether-hexane 1:3); $[\alpha]_{20}^D$ +93.1° (c, 1.00 in chloroform); $\nu_{max}$ (film) 2935, 2100 ($N_3$), 1415, 1210, 1145, 1050 and 985 cm$^{-1}$; $^1$H NMR δ 3.46 (2H, m, H-5); 3.48 (3H, s, CH$_3$); 4.32 (1H, dt, H-4); 4.47 (1H, dd, H-3, $J_{3,4}$ 7.0 Hz); 4.55, 4.74 (2H, 2×d, CH$_2$Ph, $J_{H,H'}$ 11.7 Hz); 5.13 (1H, dd, H-2, $J_{2,3}$ 4.7 Hz); 5.14 (1H, bs, H-1); 7.27–7.41 (5H, m, H-Ph). $^{13}$C NMR δ 50.55 (t, C-5); 55.91 (q, CH$_3$); 73.12 (t, CH$_2$Ph); 75.36, 79.17 (2d, C-3, C-4); 87.67 (d, C-2); 99.67 (d, C-1); 115.66 (q, CF$_3$); 127.95, 128.45, 128.70 (3d, HC-Ph); 136.35 (s, C-Ph). m/z: 236 (M+H$^-$, 100%), 68 (30%), 91 (15%). The β-anomer reacted similarly; 5-azido-3-O-benzyl-5-deoxy-β-D-xylofuranoside (11) (1.37 g, 4.89 mmol) when treated with 1.15 molar equivalent of the same reagents for the same period, afforded methyl 5-azido-3-O-benzyl-5-deoxy-2-O-trifluoromethanesulphonyl-β-D-xylofuranoside (1.57 g, 78%) as a clear oil, $R_f$ 0.70 (ether-hexane 1:3); $[\alpha]_{20}^D$ −32.0 (c, 1.1 in chloroform); $\nu_{max}$ (film) 2930, 2100 ($N_3$), 1420, 1210, 1145, 1055 and 960 cm$^{-1}$; $^1$H NMR δ 3.41, 3.57 (2H, 2×dd, H-5,5', $J_{5,5'}$ 13.0 Hz, $J_{4,5}$ 4.8 Hz, $J_{4,5'}$ 8.1 Hz); 3.47 (3H, s, CH$_3$); 4.26 (1H, dd, H-3, $J_{3,4}$ 6.3 Hz, $J_{2,3}$ 1.9 Hz); 4.44 (1H, m, H-4); 4.54, 4.76 (2H, 2×d, CH$_2$Ph, $J_{HH'}$ 11.9 Hz); 5.08 (1H, s, H-1); 5.22 (1H, bs, H-2); 7.30–7.43 (5H, m, H-Ph). m/z (NH$_3$ CI): 91 (100%), 108 (45%), 412 (M+H$^+$, 35%).

EXAMPLE 8

Methyl 3-O-Benzyl-2,5-dideoxy-25-imino-D-lyxofuranoside (13αβ)

Methyl 5-azido-3-O-benzyl-5-deoxy-2-O-trifluoromethanesulphonyl-α-D-xylofuranoside (12α) (1.60 g, 3.89 mmol) was dissolved in ethyl acetate (30 ml) and stirred under hydrogen at room temperature with 5% palladium on charcoal (200 mg) for four hours. The solution was filtered through celite, concentrated, and purified by flash chromatography (10% ethanol in dichloromethane) to yield methyl 3-O-Benzyl-2,5-dideoxy-2,5-imino-α-D-lyxofuranoside (870 mg, 95%) as a pale brown oil, which rapidly darkened. $R_f$ 0.3 (10% ethanol in dichloromethane); $v_{max}$ (film) 3420 (NH), 2940, 1450, 1245, 1170, 1025 and 640 cm$^{-1}$; $^1$H NMR δ 3.14, 3.37 (2H, 2×d, H-5,5', J$_{5,5'}$ 15.0 Hz); 3.79 (1H, s, H-2); 4.29, 4.40 (2H, 2×bs, H-3, H-4); 4.52, 4.70 (2H, 2 x d, CH$_2$Ph, J$_{H,H'}$ 12.4 Hz); 5.88 (1H, s, H-1); 6.23 (1H, bs, NH); 7.30–7.42 (5H, m, H-Ph). $^{13}$C NMR δ 49.47 (t, C-5); 55.56 (q, CH$_3$); 59.88 (d, C-2); 72.85 (t, CH$_2$Ph); 74.03, 78.32 (2d, C-3, C-4); 103.38 (d, C-1); 128.19, 128.37, 128.67 (3d, HC-Ph); 136.64 (s, C-Ph). m/z: 236 (M+H$^+$, 100%), 68 (30%), 91 (15%). Methyl 5-azido-3-O-benzyl-5-deoxy-2-O-trifluoromethanesulphonyl-β-D-xylofuranoside (12) (1.57 g, 3.82 mmol) under the same conditions gave methyl 3-O-benzyl-2,5-dideoxy-2,5-imino-β-D-lyxofuranoside (829 mg, 92.5%) after chromatography, as a rapidly darkening oil, R$_f$ 0.4 (10% ethanol in dichloromethane); $v_{max}$ (film) 3400 (NH), 2910, 1450, 1255, 1115, 1030 and 640 cm$^{-1}$; $^1$H NMR δ 3.46 (3H, s, CH$_3$); 3.48 (2H, m, H-5); 4.21, (1H, s, H-2); 4.28 (2H, bs, H-3, H-4); 4.55, 4.76 (2H, 2×d, CH$_2$Ph, J$_{H,H'}$ 12.0 Hz); 5.06 (1H, d, H-1, J$_{1,2}$ 1.9 Hz); 6.29 (1H, bs, NH); 7.33–7.38 (5H, m, H-Ph). $^{13}$C NMR δ 49.94 (t, C-5); 55.92 (q, CH$_3$); 60.50 (d, C-2); 72.58 (t, CH$_2$Ph); 76.27, 78.84 (2×d, C-3, C-4); 100.50 (d, C-1); 128.34, 128.64, (2×d, HC-Ph); 136.37 (s, C-Ph). m/z: 236 (M+H$^+$, 100%), 68 (40%), 91 (20%).

EXAMPLE 9

Methyl 3-O-benzyl-N-benzyloxycarbonyl-2,5-dideoxy-2,5-imino-D-lyxofuranoside (14αβ)

Methyl 3-O-benzyl-2,5-dideoxy-2,5-imino-α-D-lyxofuranoside (13α) (870 mg, 3.70 mmol) was stirred with a 3:2 mixture of ether and saturated aqueous sodium bicarbonate (60 ml). Benzyl chloroformate (1.57 ml, 11.1 mmol) was added to the mixture which was stirred at room temperature for 12 hours. The ether layer was separated and the aqueous phase further extracted with ether (4×25 ml). The combined extracts were dried, filtered and the solvent removed. Purification by flash chromatography (ether-hexane 1:10–1:3) afforded methyl 3-O-benzyl-N-benzyloxycarbonyl-2,5-dideoxy-2,5-imino-α-D-lyxofuranoside (1.04 g, 76%) as a white crystalline solid, m.p. 74°–75° C., R$_f$ 0.2 (ether-hexane 1:3); [α]$_{20}$$^D$ +12.0° (c, 0.98 in chloroform); $v_{max}$ (chloroform) 2940, 1695 (C=O), 1420, 1260, 1230, 1090 and 750 cm$^{-1}$; $^1$H NMR δ 3.38, 3.41 (3H, 2×s, CH$_3$); 3.3–3.7 (2H, m, 5,5'-H); 4.05–4.90 (5H, m, H-3, H-2, H-4, CH$_2$Ph); 5.12–5.20 (3H, m, H-1, CH$_2$-Z); 7.2–7.4 (10H, m, 2×H-Ph). $^{13}$C NMR δ 50.71 (t, C-5); 55.15, 55.33 (2×q, Me); 59.63, 60.17 (2×d, C-2); 66.95, 67.08 (2×t, CH$_2$-Z); 72.28 (t, CH$_2$Ph); 75.09, 75.49, 77.93, 78.48 (4×d, C-3, C-4); 105.67, 105.90 (d, C-1); 127.83, 127.92, 128.15, 128.64 (4×d, HC-Ph); 136.68, 137.46 (2×s, C-Ph); 155.68, 155.81 (2×s, C=O). m/z: 91 (100%), 108 (25%), 158 (20%), 370 (M+H$^+$, 10%). (Found C, 67.98; H, 6.39; N, 3.60. C$_{21}$H$_{23}$NO$_5$ requires C, 68.28; H, 6.28; N, 3.79). Methyl 3-O-benzyl-2,5-dideoxy-2,5-imino-β-D-lyxofuranoside (13β) (829 mg, 3.53 mmol) was treated likewise giving methyl 3-O-benzyl-N-benzyloxycarbonyl-2,5-dideoxy-2,5-imino-β-D-lyxofuranoside (1.18 g, 90%) as a clear oil, R$_f$ 0.35 (ether-hexane 1:3); [α]$_{20}$$^D$ −75.2° (c, 0.83 in chloroform); $v_{max}$ (film) 2930, 1705 (C=O), 1425, 1275, 1255, 1105 and 750 cm$^{-1}$; $^1$H NMR δ 3.36, 3.42 (3H, 2×s, CH$_3$); 3.50 (1H, 2×d 5-H); 3.67 (1H, 2×d, H-5'); 4.02–4.06 (1H, m, H-3); 4.29 (1H, bs, H-2); 4.49, 4.54 (1H, bs and dd, H-4); 4.52–4.65 (2H, m, CH$_2$Ph); 5.0–5.2 (2H, 2×dd, CH$_2$Ph); 5.21 (1H, s, H-1); 7.28–7.38 (10H, m, H-Ph). $^{13}$C NMR δ 50.02 (t, C-5); 55.70, 55.89 (2×q, Me); 60.17, 59.52 (2×d, C-2); 66.79 (t, CH$_2$-Z); 72.00, 72.10 (t, CH$_2$Ph); 77.56, 78.08, 78.52, 79.18 (4×d, C-3, C-4); 104.71, 105.11 (2×d, C-1); 128.79, 127.96, 128.33, 128.61, 128.78 (5×d, HC-Ph); 137.09, 137.22 (2×s, C-Ph); 156.20, 156.45 (2×s, C=O). m/z: 91 (100%), 370 (M+H$^+$, 60%), 202 (30%). (Found C, 68.08; H, 6.39; N, 3.40. C$_{21}$H$_{23}$NO$_5$ requires C, 68.28; H, 6.28; N, 3.79).

EXAMPLE 10

3-O-Benzyl-N-benzyloxycarbonyl-2,5-dideoxy-2,5-imino-D-lyxose (15)

Methyl 3-O-benzyl-N-benzyloxycarbonyl-2,5-dideoxy-2,5-imino-α-D-lyxofuranoside (14α) (1.015 g, 2.77 mmol) was stirred in a 1:1 mixture of trifluoroacetic acid and water (20 ml). Once all the starting material had dissolved, the solvents were evaporated (without heat) and purification by flash chromatography (ethyl acetate-hexane 1:2) gave 3-O-benzyl-N-benzyloxycarbonyl-2,5-dideoxy-2,5-imino-D-lyxose (901 mg, 92%) as a clear oil, [α]$_{20}$$^D$ −24.2° (c, 1.39 in chloroform); $v_{max}$ (film) 3400 (OH), 1700 (2×CO), 1425, 1360, 1195 and 700 cm$^{-1}$; δ$_H$ 2.55 (1H, bs, OH); 3.65 (1H, 2×d, H-5); 3.79 (1H, 2×dd, H-5'); 4.03, 4.31 (2H, 2×bs, H-2, H-3); 4.44, 4.55 (1H, bs and dd, H-4); 4.51–4.71 (2H, m, CH$_2$Ph); 5.09–5.20 (2H, m, CH$_2$-Z); 7.29–7.40 (10H, m, H-Ph); 9.49, 4.59 (1H, 2×d, H-1, J$_{1,2}$ 0.7 Hz). m/z: 91 (100%), 108 (68%), 230 (50%), 356 (M+H$^+$, 20%). (Found C, 67.76; H, 6.48; N, 3.77. C$_{20}$H$_{21}$NO$_5$ requires C, 67.59; H, 5.96; N, 3.94). Methyl 3-O-benzyl-N-benzyloxycarbonyl-2,5-dideoxy-2,5-imino-β-D-lyxofuranoside (14β) (976 mg, 2.64 mmol) reacted similarly; it afforded the title compound (15) (820 mg, 87%), spectroscopically identical to that prepared above, under the same reaction conditions.

EXAMPLE 11

2-O-Benzyl-N-benzyloxycarbonyl-1,4-deoxy-1,4-imino-D-arabinitol (16)

A solution of 3-O-benzyl-N-benzyloxycarbonyl-2,5-dideoxy-2,5-imino-D-lyxose (15) (506 mg, 143 mmol) in ethanol was treated with a suspension of sodium borohydride (38.9 mg, 0.75 meq) in ethanol-water 1:1 (2 ml). After 15 minutes, excess ammonium chloride was added and the solution concentrated by evaporation, then partitioned between water (10 ml) and dichloromethane (10 ml). The aqueous layer was further extracted with dichloromethane (4×10 ml), and the combined organic layers dried, filtered and evaporated to give 2-O-benzyl-N-benzyloxycarbonyl-1,4-deoxy-1,4-imino-D-arabinitol, (501 mg, 98%) as a colourless oil, [α]$_{20}$$^D$ −16.4° (c, 1.26 in chloroform); $v_{max}$ (film) 3360 (OH), 2930, 1670 (CO), 1430, 1355, 1090 and 700 cm$^{-1}$; $^1$H NMR δ (poorly resolved due to rotameric exchange) 1.9 (1H, bs, OH); 3.50–4.25 (7H, m, H-1,1',2,3,4,5,5'); 4.60 (2H, s, CH$_2$Ph); 5.90, 5.17 (2H, 2×d, CH$_2$-Z. J$_{H,H'}$12.5 Hz); 7.29–7.41 (10H, m, H-Ph). m/z: 358 (M+H$^+$, 100%), 250 (M-PhCH$_2$O$^-$, 80%), 91 (80%), 314 (35%). $^{13}$C NMR δ 54.63 (t, C-1); 62.36 (t, C-5); 65.12 (d, C-4); 67.12 (t, CH$_2$-Z); 71.55 (t, CH$_2$Ph); 72.64 (d, C-2); 86.49 (d, C-3); 127.07, 127.83, 128.01, 128.13, 128.45, 128.70 (6×d, HC-Ph); 136.49, 137.54 (2×s, C-Ph); 156.19 (s, C=O). (Found C, 66.90; H, 6.23; N, 3.61. C$_{20}$H$_{23}$NO$_5$ requires C, 67.21; H, 6.47; N, 3.92).

EXAMPLE 12

1,4-Dideoxy-1,4-imino-D-arabinitol (1)

2-O-Benzyl-N-benzyloxycarbonyl-1,4-deoxy-1,4-imino-D-arabinitol (16) (483 mg, 1.35) was dissolved in acetic acid (8 m) and stirred under hydrogen at atmosphere pressure with palladium black (150 mg). After 18 hours, the catalyst was removed by filtration and the solvent removed. Purification by flash chromatography (CMAW) and ion exchange chromatography afforded, 1,4-dideoxy-1,4-imino-D-arabinitol, (224 mg, 97.6%) as its hydrochloride salt, a white crystalline solid, m.p. 111°–113° C., [lit.[12] 113°–115° C.], $[\alpha]_{20}^D$ +36.7° (c, 1.255 in water) [lit.[12] 37.9° (c, 0.53 in water)]: $\nu_{max}$ (KBr disc) 3350, 1575, 1405, 1265, 1080, 1019, 1045 and 970 cm$^{-1}$; $^1$H NMR (D$_2$O) δ 3.20, 3.42 (1H, 2×dd, H-1,1', $J_{1,1'}$12.5 Hz, $J_{1,2}$2.4 Hz, $J_{1',2}$ 4.6 Hz); 3.47 (1H, dd, H-4, $J_{4,5}$8.4 Hz, $J_{4,5'}$4.3 Hz); 3.67, 3.80 (2H, 2×dd, H-5,5'); 3.93 (1H, t, H-3, $J_{2,3}$3.4 Hz); 4.17 (1H, m, H-2). $^{13}$C NMR (D$_2$O) δ 50.80 (t, C-1); 59.64 (t, C-5); 67.30 (t, C-4); 75.03, 76.50 (2×d, C-3, C-2). m/z: 102 (M-CHO$^+$, 100%), 55 (30%), 134 (M+H$^+$, 17%).

EXAMPLE 13

(2S, 3R, 4R)-3-Benzyl-N-benzyloxycarbonyl-4-hydroxyproline (17)

A solution of 3-O-benzyl-N-benzyloxycarbonyl-2,5-dideoxy-2,5-imino-D-lyxose (15) (900 mg, 2.54 mmol), in a 1:1 mixture of water and 1,4-dioxan (15 ml) containing barium carbonate (1.46 g, 7.62 mmol), was cooled to 0° C. and treated with bromine (298 μl, 5.33 mmol). After stirring for 24 hours excess bromine was destroyed by the dropwise addition of 10% sodium thiosulphate solution and the suspension acidified with 2M HCl (20 ml). The product was extracted into dichloromethane (4×50 ml), dried, filtered and evaporated. Purification by flash chromatography (ethyl acetate-hexane (1:1 to ethyl acetate) afforded (2S,3R,4R)-3-benzyl-N-benzyloxycarbonyl-4-hydroxyproline (738 mg, 75%) as a clear oil, $[\alpha]_{20}^D$ −3.7° (c, 0.88 in chloroform); $\nu_{max}$ (film) 3400 (OH), 2950, 1680 (2×CO), 1425, 1360 and 1195 cm$^{-1}$; $^1$H NMR δ 3.62–3.78 (2H, 2×dd, H-5); 4.21, 4.26 (2H, s, and bs, H-3, H-2); 4.49–4.69 (3H, m, C$\underline{H}_2$Ph); 5.06–5.18 (2H, 2×dd, C$\underline{H}_2$-Z); 5.6 (2H, bs, 2×OH); 7.27–7.38 (10H, m, 2×H-P$\overline{h}$). m/z: 91 (100%), 310 (45%), 372 (M+H$^+$, 30%).

EXAMPLE 14

(2S, 3R, 4R)-3,4-Dihydroxyproline (2)

(2S, 3R, 4R)-3-benzyl-N-benzyloxycarbonyl-4-hydroxyproline (17) (523 mg, 1.95 mmol) was dissolved in glacial acetic acid (12 ml) containing palladium black (100 mg) and stirred under hydrogen at atmospheric pressure for 48 hours. The solution was filtered and the solvent removed. Purification by flash chromatography (CMAW) and ion exchange resin gave (2S, 3R, 4R)-3,4-dihydroxyproline (220 mg, 93.5%) as a white crystalline solid, m.p. 220°–245° C. decomposed without melting (lit.[37] 250° dec.), $[\alpha]_{20}^D$ −12.2° (c, 0.83 in water) [lit.[37] $[\alpha]_D^{25}$ −19° (c, 0.4 in water)]; $\nu_{max}$ (KBr disc) 3260, 1615 (CO), 1370, 1270, 1075, 1050 and 760 cm$^{-1}$; $^1$H NMR δ (D$_2$O) 3.35 (1H, d, H-5, $J_{5,5'}$12.5 Hz); 3.44 (1H, dd, H-5', $J_{4,5'}$3.7 Hz); 3.90 (1H, s, H-2); 4.14 (1H, dt, H-4, $J_{3,4\ 1,2}$ Hz); 4.36 (1H, bs, H-3). $^{13}$C NMR (D$_2$O) δ 51.71 (t, C-5); 66.33 (d, C-2); 74.75 (d, C-4); 79.14 (d, C-3); 171.86 (s, C-1). m/z: 124 (100%), 104 (77%), 148 (M+H$^+$, 75%), 84 (67%).

EXAMPLE 15

3-O-Benzyl-1,2-O-isopropylidene-5-O-trifluoromethanesulphonyl-α-D-xylofuranose (18)

A solution of 3-O-benzyl-1,2-O-isopropylidene-α-D-xylofuranose (8) (2.00 g, 7.14 mmol) in dry dichloromethane (25 ml) was treated with dry pyridine (1.15 ml, 14.3 mmol) and cooled to −50° C. under nitrogen. Trifluoromethanesulphonyl chloride (1.45 ml, 1.45 ml, 8.57 mmol) was added and the stirred solution allowed to warm to −30° C. over 1 hour. Methanol (0.5 ml) was added, the solution warmed to room temperature and the solvents removed to give a waxy yellow solid. Ice cold ether (10 ml) was added and the mixture filtered, washing the solid with further ether (3×5 ml). The ether was evaporated yielding a yellow oil. This was purified by flash chromatography (eluting with ether-hexane 1:5) to give 3-O-benzyl-1,2-O-isopropylidene-5-O-trifluoromethanesulphonyl-α-D-xylofuranose (2.76 g, 94%) an unstable colourless oil used immediately in the next step, $\nu_{max}$ (film) 2920, 1415, 955 and 700 cm$^{-1}$; $^1$H NMR δ 1.26, 1.42 (6H, 2×s, acetonide); 3.99 (1H, dd, H-3, $J_{2,3}$1.2 Hz, $J_{3,4}$3.3 Hz, 4.00–4.65 (6H, m, H-2, H-4, H-5,5', C$\underline{H}_2$Ph); 5.96 (1H, d, H-1, $J_{1,2}$4.8 Hz); 7.25–7.40 (5H, m, H-Ph). m/z: 4.30 (M+NH$_4^-$, 100%) 372 (M-(CH$_3$)$_2$CO+NH$_4^-$, 25%), 91 (50%).

EXAMPLE 16

3-O-Benzyl-5-cyano-5-deoxy-1,2-O-isopropylidene-α-D-xylofuranose (19)

Finely ground, dry potassium cyanide (4.39 g, 67.6 mmol) was added to a stirred solution of 3-O-benzyl-1,2-O-isopropylidene-5-O-trifluoromethanesulphonyl-α-D-xylofuranose (18) (9.28 g, 22.5 mmol) in dry DMf (100 ml) and stirred vigorously at 30° C. for 6 hours. Most of the solvent was removed by evaporation and the resulting oil partitioned between dichloromethane (100 ml) and water (100 ml). The aqueous phase was extracted with dichloromethane (3×100 ml) and the combined organic layers washed with brine (50 ml), dried, filtered and concentrated to a viscous oil. Purification using flash chromatography (25% ether in hexane) gave 3-O-benzyl-5-cyano-5-deoxy-1,2-O-isopropylidene-α-D-xylofuranose (6.28 g, 96%) as a white crystalline solid, m.p. 86°–87° C., $[\alpha]_{20}^D$ −85.2° (c, 0.41 in chloroform); $\nu_{max}$ (chloroform) 2980, 2245 (CN), 1450 and 1165 cm$^{-1}$ $^1$H NMR δ 1.34, 1.51 (6H, 2×s, acetonide); 2.74 (2H, d, H-5,5'); 4.01 (1H, d, H-3); 4.50 (1H, dd, H-4, $J_{3,4}$3.3 Hz, $J_{4,5}$7.1 Hz); 4.58, 4.73 (1H, d, C$\underline{H}_2$Ph, $J_{H,H'}$11.5 Hz); 4.65 (1H, d, H-2); 5.92 (1H, d, H-1, $J_{1,2}$3.7 Hz); 7.30–7.41 (5H, m, H-Ph). $^{13}$C NMR δ 26.28, 26.87 (2×q, CH$_3$-acetonide); 72.64 (t, CH$_2$Ph); 72.64, 81.76, 82.17 (3×d, C-2,3,4); 105.37 (d, C-1); 112.18 (s, acetonide); 116.83 (s, CN); 127.96, 128.28, 128.66 (3×d, HC-Ph); 136.97 (s, C-Ph); m/z: 91 (100%), 290 (M+H$^-$, 65%), 307 (M+NH$_4^+$, 70%). (Found C, 66.13; H, 6.90; N, 4.58. C$_{16}$H$_{19}$NO$_4$ requires C, 66.42; H, 6.62; 4.84).

EXAMPLE 17

Methyl 3-O-Benzyl-5-cyano-5-deoxy-D-xylofuranoside (20αβ)

A solution of 3-O-benzyl-5-cyano-5-deoxy-1,2-O-isopropylidene-α-D-xylofuranose (19) (6.01 g, 20.8 mmol)

was dissolved in dry methanol (150 ml) containing acetyl chloride (11.8 g, 0.15 mol) and stood at −5° C. for 12 hours. The solution was basified (Na$_2$CO$_3$), concentrated and partitioned between water (150 ml) and dichloromethane (150 ml). The light brown aqueous phase was extracted further with dichloromethane (3×150 ml) and the combined extracts washed with brine (30 ml), dried (Na$_2$SO$_4$), filtered and evaporated to give an oil. Flash chromatography (ether-hexane 3:1 to 1:1), gave methyl 3-O-benzyl-5-cyano-5-deoxy-D-xylofuranoside (4.44 g, 81%) as a partially separated 4:3 mixture of anomers.

α-anomer, m.p. 59°–60° C., R$_f$0.2 (ether-hexane 1:1); [α]$_{20}^D$+67.2° (c, 0.81 in chloroform); ν$_{max}$3450, 2940, 2230 (CN), 1455, 1110 and 1045 cm$^{-1}$; $^1$H NMR δ 2.66 (1H, d, OH, J$_{OH,2}$5.1 Hz); 2.66, 2.72 (2H, 2×d, H-5,5′, J$_{4,5}$7.6 Hz); 3.50 (3H, s, CH$_3$); 4.02 (1H, dd, H-3, J$_{2,3}$4.0 Hz, J$_{3,4}$6.0 Hz); 4.30 (1H, m, H-2); 4.46 (1H, dt, H-4); 4.60, 4.81 (1H, d, CH$_2$Ph, J$_{H,H'}$11.75 Hz); 4.99 (1H, d, H-1, J$_{1,2}$4.5 Hz); 7.31–7.38 (5H, m, H-Ph). $^{13}$C NMr δ 18.99 (t, C-5); 55.88 (q, CH$_3$); 71.66 (t, CH$_2$Ph); 73.83, 76.64, 82.59, (3×d, C-2, C-3, C-4); 101.79 (d, C-1); 117.49 (s, CN); 127.70, 127.87 128.40 (3×d, HC-Ph); 137.25 (s, C-Ph). m/z: 91 (100%), 281 (M+NH$_4^+$, 65%), 264 (M+H$^+$, 25%). (Found C, 64.13; H, 6.70; N, 5.51. C$_{14}$H$_{17}$NO$_4$ requires C, 63.87; H, 6.51; N, 5.32).

β-anomer, colourless oil, R$_f$0.18 (ether-hexane 1:1 ); [α]$_{20}^D$ −64.5° (c, 0.895 in chloroform); ν$_{max}$ (film) 3440 (OH), 2920, 2250 (CN), 1450, 1100 and 1040 cm$^{-1}$; $^1$H NMR δ 2.62, 2.77 (2H, 2×dd, H-5,5′, J$_{5,5'}$15.7 Hz, J$_{4,5}$4.7 Hz, J$_{4,5'}$7.5 Hz); 2.71 (1H, s, OH); 3.42 (3H, s, CH$_3$); 4.00 (1H, dd, H-3, J$_{4,5'}$2.8 Hz, J$_{3,4}$6.3 Hz); 4.23 (1H, bs, H-2); 4.55 (1H, m, H-4); 4.57, 4.71 (2H, 2×d, CH$_2$Ph, J$_{H,H'}$11.9 Hz); 4.81 (1H, d, H-1, J$_{1,2}$1.3 Hz); 7.27–7.41 (5H, m, H-Ph). −C NMR δ 20.24 (t, C-5); 55.80 (q, Me); 72.76 (t, CH$_2$Ph); 76.66, 79.38 (2×d, C-3, C-4); 83.49 (d, C-2); 110.11 (d, C-1); 118.19 (s, CN); 128.25, 128.38, 128.81 (3×d, HC-Ph); 137.41 (s, C-Ph). (Found C, 63.63; H, 6.77; N, 5.14.

EXAMPLE 18

Methyl 3-O-Benzyl-5-cyano-5-deoxy-2-O-trifluoromethanesulphonyl-D-xylofuranoside (21α).

A 4:3 mixture of the α and β anomers of methyl 3-O-benzyl-5-cyano-5-deoxy-D-xylofuranoside (20αβ) (4.23 g, 16.1 mmol) was dissolved in dry dichloromethane and cooled to −50° C. under nitrogen. Dry pyridine (3.11 ml, 3.06 g, 38.6 mmol) and trifluoromethanesulphonic anhydride (3.25 ml, 5.45 g, 19.3 mmol) were added and the stirred solution allowed to warm to 0° C. over 90 minutes. Methanol (1 ml) was added and the solvents removed. The residue was dissolved in ether (50 ml), filtered, and evaporated to give a yellow oil. Purification by flash chromatography (ether-hexane 1:10 to 1:3) gave the partially separated title compounds (β:α 4:3) (6.04 g, 95%).

α-anomer, a colourless oil, R$_f$0.1 (ether-hexane 1:4); [α]$_{20}^D$ +87.8° (c, 1.15 in chloroform); ν$_{max}$ (film) 2940, 2250 (CN), 1410, 1245, 1150, 1040 and 990 cm$^{-1}$; $^1$H NMR δ 2.66 (2H, s, H-5,5′); 3.48 (3H, s, CH$_3$); 4.46–4.48 (2H, m, H-3, H-4); 4.57, 4.76 (2H, 2×d, CH$_2$Ph, J$_{H,H'}$ 11.6 Hz); 5.11 (1H, dd, H-2, J$_{1,2}$0.8 Hz, J$_{2,3}$1.2 Hz); 5.12 (1H, bs, H-1); 7.34–7.39 (5H, m, H-Ph). $^{13}$C NMR δ 19.00 (t, C-5); 56.05 (q, Me); 72.54, 78.95 (2×d, C-3, C-4); 72.54 (t, CH$_2$Ph); 87.39 (d, C-2); 99.95 (d, C-1); 116.92 (s, CN); 118.56 (q, CF$_3$); 128.24, 128.74, 128.92 (3×d, HC-Ph); 136.10 (s, C-Ph). (Found C, 45.58; H, 4.08; N, 3.54. C$_{15}$H$_{16}$NO$_6$SF$_3$ requires C, 45.63; H, 4.01; N, 3.69).

β-anomer, m.p. 59°–60° C., R$_f$0.18 (ether-hexane 1:4); [α]$_{20}^D$ −59.4° (c, 1.085 in chloroform); ν$_{max}$ (chloroform) 2930, 2250 (CN), 1420, 1245, 1155, 1045 and 955 cm$^{-1}$; $^1$H NMR δ 2.70, 2.79 (2H, 2×dd, H-5,5′, J$_{5,5'}$ 16.7 Hz, J$_{4,5}$ 6.5 Hz, J$_{4,5'}$ 7.9 Hz); 3.47 (3H, s, CH$_3$); 4.29 (1H, dd, H-3, J$_{2,3}$ 1.6 Hz, J$_{3,4}$ 6.3 Hz); 4.58, 4.78 (2H, 2×d, CH$_2$Ph, J$_{H,H'}$ 11.8 Hz); 4.63 (1H, m, H-4); 5.08 (1H, s, H-1); 5.20 (1H, bs, H-2); 7.34–7.41 (5H, m, H-Ph). $^{13}$C NMR δ 20.16 (t, C-5); 56.03 (q, Me); 73.41 (t, CH$_2$Ph); 77.16, 80.85 (2×d, C-3, C-4); 90.65 (d, C-2); 106.70 (d, C-1); 116.8 (s, CN); 117.64 (q, CF$_3$); 128.20, 128.67, 128.79 (3×d, HC-Ph); 135.85 (s, C-Ph). m/z:413 (M+NH$_4^+$, 100%), 174 (35%), 91 (40%). (Found C, 45.42; H, 4.17; N, 3.18. C$_{15}$H$_{16}$NO$_6$SF$_3$ requires C, 45.63; H, 4.01; N, 3.69).

EXAMPLE 19

Methyl 3-O-Benzyl-2,6-imino-2,5,6-trideoxy-D-lyxo-hexofuranoside (22αβ)

A 1:2 mixture of the α and β anomers of methyl 3-O-benzyl-5-cyano-5-deoxy-2-O-trifluoromethanesulphonyl-D-xylofuranoside (21αβ) (2.51 g, 6.36 mmol) dissolved in cyclohexane (200 ml) at 40° C. was treated with borane-dimethyl sulphide complex (10M in THF, 955 μl, 9.55 mmol) then stirred at room temperature overnight. Methanol (1 ml) was added, and the solvents evaporated then replaced with a 1:1 mixture of methanol and pyridine (50 ml). This was stirred with potassium carbonate (5 g) at room temperature for 48 hours. The solvents were removed and the residue dissolved in dichloromethane (20 ml), filtered and concentrated by evaporation. Purification using flash chromatography produced methyl 3-O-benzyl-2,6-imino-2,5,6-trideoxy-D-lyxohexofuranoside (α:β 1:2) (1.52 g, 96%) as a partially separated mixture of colourless oils which rapidly turn brown on storage.

α-anomer, R$_f$0.30 (10% ethanol in dichloromethane); [α]$_{20}^D$ +20.7° (c, 1.35 in chloroform); ν$_{max}$ (film) 2920, 1440, 1250, 1160, 1030 and 640 cm$^{-1}$; $^1$H NMR δ 1.55–1.65 (1H, m, H-5); 2.05–2.20 (1H, m, H-5); 3.11, 3.43 (2H, 2×dd, H-6,6′, J$_{6,6'}$ 9.0 Hz); 3.41 (1H, s, CH$_3$); 3.73 (1H, d, H-2, J$_{2,3}$ 9.2 Hz); 3.75 (1H, bs, NH); 4.26 (1H, dd, H-3, J$_{3,4}$ 6.0 Hz); 4.38–4.42 (1H, m, H-4); 4.58, 4.72 (2H, 2×d, CH$_2$Ph, J$_{H,H'}$ 12 Hz); 5.19 (1H, s, H-1); 7.30–7.40 (5H, m, H-Ph). $^{13}$C NMR δ 25.89 (t, C-5); 38.86 (t, C-6); 55.29 (q, Me); 58.81 (d, C-2); 72.12 (t, CH$_2$Ph); 74.30, 75.36 (2×d, C-3, C-4); 104.91 (d, C-1); 127.73, 128.04, 128.54 (3×d, HC-Ph); 137.83 (s, C-Ph). m/z:91 (100%), 108 (55%), 250 (M+H$^+$, 30%).

β-anomer; R$_f$0.25 (10% ethanol in dichloromethane); [α]$_{20}^D$ −63.2° (c, 1.25 in chloroform); ν$_{max}$ (film) 3040, 1455, 1255, 1085, 1030 and 640 cm$^{-1}$; $^1$H NMR δ 1.71–1.80 (1H, m, H-5); 2.16–2.63 (1H, m, H-5′); 3.43, 3.71 (2H, 2×dd, H-6,6′, J$_{6,6'}$ 8,0 Hz); 3.53 (1H, s, CH$_3$); 3.99, 4.01 (2H, 2×s, H-2, H-3); 4.28–4.31 (1H, m, H-4); 4.60, 4.87 (2H, 2×d, C$_2$HPh, J$_{H,H'}$ 12 Hz); 5.15 (1H, d, H-1, J$_{1,2}$ 2.8 Hz); 6.2 (1H, bs, NH); 7.30–7.40 (5H, m, H-Ph). $^{13}$C NMR δ 24.71 (t, C-5); 38.49 (t, C-6); 55.21 (q, Me); 56.71 (d, C-2); 71.80 (t, CH$_2$Ph); 74.79, 75.00 (2×d, C-3, C-4); 103.25 (d, C-1); 127.70, 127.92, 128.55 (3×d, HC-Ph); 137.45 (s, C-Ph). m/z:250 (M+H$^-$, 100%), 98 (40%).

EXAMPLE 20

Methyl 3-O-Benzyl-N-benzyloxycarbonyl-2,6-imino-2,5,6-trideoxy-D-lyxo-hexofuranoside (23αβ)

Benzyl chloroformate (1.30 ml, 9.17 mmol) was added to a solution of methyl 3-O-benzyl-2,6-imino-2,5,6-trideoxy-D-lyxo-hexofuranoside epimers (22αβ) (α:β 1:2) (1.52 g, 6.11 mmol), in a stirred 3:2 mixture of ether and saturated sodium bicarbonate (60 ml). After 18 hours the ether layer was removed and the aqueous phase extracted further with ether (3×50 ml). The combined ether extracts were dried, filtered and evaporated. Purification by flash chromatography afforded both the methyl 3-O-Benzyl-N-benzyloxycarbonyl-2,6-imino-2,5,6-trideoxy-D-lyxo-hexofuranoside anomers as clear oils.

α-anomer (612 mg, 26%), $R_f$ 0.65 (ether-hexane 1:1); $[\alpha]_{20}^D$ −12° (c, 0.7 in chloroform); $\nu_{max}$ (film) 1695, 1430, 1260, 1105 and 1040 cm$^{-1}$; $^1$H NMR δ 1.55–1.68 (1H, m, H-5); 2.08–2.22 (1H, m, H-5′); 3.16–3.22 (1H, m, H-6); 3.40, 3.41 (3H, 2×s, CH$_3$); 4.04–4.21 (2H, m, H-6′, H-3); 4.40–4.59 (2H, m, H-2, H-4); 4.70, 4.72 (2H, 2×s, CH$_2$Ph); 5.01, 5.08 (2H, dd, CH$_2$-Z, $J_{H,H'}$ 3.4 Hz); 5.13, 5.15, (1H, 2×s, H-1); 7.20–7.39 (10H, m, 2×H-Ph). $^{13}$C NMR δ 24.54 (t, C-5); 38.33 (t, C-6); 55.27 (q, Me); 56.83, 57.33 (2×d, C-2); 67.51 (t, CH$_2$-Z); 72.13, 72.40 (2×t, CH$_2$Ph); 74.51 (d, C-3, C-4); 104.75, 105.24 (2×d, C-1); 127.20, 127.70, 128.05, 128.52 (4×d, HC-Ph); 136.48 (s, C-Ph). m/z:91 (100%), 108 (47%), 250 (20%), 384 (M+11+, 15%). (Found C, 68.60; H, 6.72; N, 3.69. C$_{22}$H$_{25}$NO$_5$ requires C, 68.91; H, 6.57; N, 3.65).

β-anomer (1.25 g, 53%), $R_f$ 0.35 (ether-hexane 1:1); $[\alpha]_{20}^D$ −63.0° (c, 1.25 in chloroform); $\nu_{max}$ (film) 1695, 1430, 1220, 1110 and 1030 cm$^{-1}$; $^1$H NMR δ 1.54–1.64 (1H, m, H-5); 2.03–2.14 (1H, m, H-5′); 3.47, 3.48 (3H, 2×s, CH$_3$); 3.50–3.61 (1H, m, H-6); 3.83–4.09 (2H, m, H-6′, H-3); 4.33–4.92 (4H, m, H-2, H-4, CH$_2$Ph); 5.02–5.23 (3H, m, H-1, CH$_2$-Z); 7.21–7.39 (10H, m, 2×H-Ph). m/z:91 (100%), 108 (45%), 188 (17%), 384 (M++, 12%). $^{13}$C NMR δ 23.96 (t, C-5); 38.63 (t, C-6); 53.88, 54.41 (2×q, Me); 56.46 (d, C-2); 67.03 (t, CH$_2$-Z); 71.65 (t, CH$_2$Ph); 73.39, 75.36 (2×d, C-3, C-4); 102.82, 103.30 (2×d, C-1); 127.40; 127.58, 127.73, 127.80, 127.96, 128.43 (6×d, HC-Ph); 136.00 (s, C-Ph); 155.35 (s, C=O). (Found C, 68.75; H, 7.14; N, 3.43. C$_{22}$H$_{25}$NO$_5$ requires C, 68.91; H, 6.57; N, 3.65).

EXAMPLE 21

3-O-Benzyl-N-benzyloxycarbonyl-2,6-imino-2,5,6-trideoxy-D-lyxo-hexose (24)

A solution of methyl 3-O-benzyl-2,6-imino-2,5,6-trideoxy-β-D-lyxo-hexofuranoside (23β) (762 mg, 2.06 mmol) in a 1:1 mixture of trifluoroacetic acid and water (20 ml) was stirred at room temperature for 20 minutes. The solvents were removed in vacuo and the crude material purified by flash chromatography (ethyl acetate-hexane 1:2) to give 3-O-benzyl-N-benzyloxycarbonyl-2,6-imino-2,5,6-trideoxy-D-lyxo-hexose (640 mg, 87%) as a clear oil, $[\alpha]_{20}^D$ −17.2° (c, 0.73 in chloroform); $\nu_{max}$ (film) 3400 (OH), 2920, 1690 (C=O), 1410, 1345 and 1060 cm$^{-1}$; $^1$H NMR δ 1.50–1.71 (1H, m, H-5); 1.80 (1H, bs, OH); 2.02–2.20 (1H, m, H-5′); 3.08–3.27 (1H, m, H-6); 3.94–4.20 (2H, m, 6-H, H-3); 4.25–4.85 (4H, m, H-2, H-4, CH$_2$-Ph); 5.05–5.18 (2H, m, CH$_2$-Z); 5.50, 5.53 (0.75H, 2×s, H-1-hemiacetal); 7.20–7.40 (10H, m, 2×H-Ph); 9.68 (0.25H, s, H-1-aldehyde). $^{13}$C NMR δ 24.17 (t, C-5); 38.10 (t, C-6); 57.26, 57.77 (2×d, C-2); 67.30, 67.48, 67.58 (3×t, CH$_2$-Z); 71.38, 71.84, 72.12 (3×t, CH$_2$Ph); 74.00, 74.63, 74.76 (3×d, C-3, C-4); 98.72, 98.88, 198.17 (3×d, C-1); 127.35, 127.58, 127.85, 128.01, 128.23, 128.63 (6×d, HC-Ph); 136.51, 136.62, 136.73, 137.46, 155.60 (s, C=O-Z); 137.74, 137.88 (6×s, C-Ph). m/z: 91 (100%), 262 (20%), 370 (M+H+, 15%). (Found C, 68.68; H, 6.40; N, 3.71. C$_{21}$H$_{23}$NO$_5$ requires C, 68.28; H, 6.28; N, 3.79).

Methyl 3-O-benzyl-2,6-imino-2,5,6-trideoxy-β-D-lyxo-hexofuranoside (23α) (606 mg, 164 mmol) afforded the title compound (513 mg, 83%), spectroscopically identical to that produced above, under the same conditions.

EXAMPLE 22

4-O-Benzyl-N-benzyloxycarbonyl-1,5-imino-1,2,5-trideoxy-D-arabino-hexitol (25)

3-O-Benzyl-N-benzyloxycarbonyl-2,6-imino-2,5,6-trideoxy-D-lyxo-hexose (24) (364 mg, 0.986 mmol) was dissolved in ethanol (5 ml) and treated with a solution of sodium borohydride (30.0 mg, 0.784 mmol) in a 1:1 mixture of EtOH and H$_2$O (2 ml). After 20 minutes excess ammonium chloride was added, the solution concentrated, poured into brine (15 ml) and extracted with dichloromethane (4×20 ml). The organic layers were combined, dried, filtered and evaporated to give 4-O-benzyl-N-benzyloxycarbonyl-1,5-imino-1,2,5-trideoxy-D-arabino-hexitol (355 mg, 97%) as a clear oil, $[\alpha]_{20}^D$ −36.7° (c, 0.22 in chloroform); $\nu_{max}$ (film) 3380 (OH), 2910, 1665 (2×CO), 1430, 1210 and 1075 cm$^{-1}$; $^1$H NMR δ 1.55–1.68 (1H, m, H-2); 2.04–2.17 (1H, m, H-2′); 2.85 (2H, bs, 2×OH); 3.40–3.57 (2H, m, H-5, H-1); 3.83–4.03 (4H, m, 6,6′-H, H-4, H-1′); 4.34 (1H, bs, H-3); 4.55, 4.72 (2H, 2×d, CH$_2$Ph, $J_{H,H}$ 12.0 Hz); 5.15 (2H, s, CH$_2$-Z); 7.28–7.38 (10, m, 2×H-Ph). m/z: 264 (M-benzyloxy$^-$, 100%), 91 (10%), 372 (M+H$^-$, 5%).

EXAMPLE 23

Fagomine, [1,5-Imino-1,2,5-trideoxy-D-arabino hexitol] (3)

4-O-Benzyl-N-benzyloxycarbonyl-1,5-imino-1,2,5-trideoxy-D-arabino-hexitol (25) (325 mg, 0.877 mmol) was dissolved in acetic acid (8 ml) and stirred under hydrogen at atmospheric pressure with palladium black (100 mg). After 18 hours, the solution was filtered and evaporated. Subsequent purification by flash chromatography (CMAW) and ion exchange gave 1,5-imino-1,2,5-trideoxy-D-arabino-hexitol as the hydrochloride salt (158 mg, 98%) a white crystalline solid, m.p. (methanol-ether) 173°–175° C., $[\alpha]_{20}^D$ +17.9° (c, 0.78 in water); $\nu_{max}$ (KBr disc) 3370, 1615, 1390, 1055, 935 and 660 cm$^{-1}$; $^1$H NMR (D$_2$O) δ 1.58 (1H, dddd, H-2, $J_{2,2'}$ 14.2 Hz, $J_{2,3}$ 11.4 Hz, $J_{2,1}$ 13.6 Hz, $J_{2,1'}$ 4.6 Hz); 2.06 (1H, dddd, $J_{2',1'}$ 2.4 Hz, $J_{2',3}$ 4.8 Hz, $J_{2',1}$ 3.2 Hz); 2.90–3.01 (2H, m, H-5, H-1); 3.30 (1H, ddd, H-1′, $J_{1,1'}$ 13.2 Hz); 3.38 (1H, dd, H-4, $J_{3,4}$ 9.2 Hz, $J_{4,5}$ 10.5 Hz); 3.57 (1H, ddd, H-3); 3.73, 3.79 (2H, 2×dd, H-6,6′, $J_{6,6'}$ 12.7 Hz, $J_{5,6}$ 5.2 Hz, $J_{5,6'}$ 3.4 Hz). $^{13}$C NMR δ 29.33 (t, C-2); 42.66 (t, C-1); 58.53 (t, C-6); 60.68 (d, C-5); 70.39, 71.24 (2×d, C-3, C-4). m/z: 148 (M+H$^-$, 100%), 116 (10%), 72 (8%). Also characterized as free base, m.p. (acetone-water) 178°–180° C., [lit.[20] 180°–184° C.], $[\alpha]_{20}^D$ +21.0° (c 0.3 in water) [lit.[20] +24.7 (c 0.4 in water)]; $^1$H NMR δ 1.28 (1H, dddd, H-2), 1.81 (1H, dddd, H-2′), 2.40 (1H, ddd, H-1), 2.83 (1H, ddd, H-1′), 2.99 (1H, dd, H-4), 3.37 (1H, m, H-3), 3.46 (1H, dd, H-6), 3.68 (1H, dd, H-6′;

13C NMR δ 33.45 (t, C-2), 43.30 (t, C-1), 61.59 (d, C-5), 62.45 (t, C-6), 73.98 (2×d, C-3,4).

EXAMPLE 24

3-O-Benzyl-N-benzyloxycarbonyl-2,6-imino-2,5,6-trideoxy-D-lyxo-hexono-1,4-lactone (26)

A solution of 1,5-imino-1,2,5-trideoxy-D-arabino-hexitol (24) (407 mg, 1.10 mmol) in a 1:3 mixture of water and 1,4-dioxan containing barium carbonate (653 mg, 3.31 mmol), was cooled to 0° C. and treated with bromine (70 μl, 221 mg, 1.37 mmol), then stirred at room temperature for 24 hours. Sodium thiosulphate solution (1M, aqueous) was added until the bromine was removed then the solution acidified with hydrochloric acid (2M, aq, 30 ml) and centrifuged. The supernatent was removed and extracted with ethyl acetate (4×20 ml). The combined organic phase was dried, filtered and evaporated. Purification by flash chromatography gave 3-O-benzyl-N-benzyloxycarbonyl-2,6-imino-2,5,6-trideoxy-D-lyxo-hexono-1,4-lactone (342 mg, 84%) as a clear oil, $[\alpha]_{20}^D$ −13.7° (c, 1.42 in chloroform); $\nu_{max}$ (film) 3030, 2880, 1790 (lactone CO), 1700 (Z CO), 1425, 1260, 1170, 1060, and 700 cm$^{-1}$; 1H NMR δ 1.80–1.93 (1H, m, H-5); 2.28–2.35 (1H, m, H-5'); 3.15–3.20 (1H, m, H-6); 3.93–4.07 (1H, m, H-6'); 4.15, 4.28 (1H, 2×dd, H-3); 4.39–4.61 (2H, m, H-2, H-4); 4.74–4.83 (2H, m, CH$_2$Ph; 5.04–5.20 (3H, m, H-1, CH$_2$-Z), 7.17–7.35 (10H, m, 2×H-Ph). 13C NMR δ 26.25 (t, C-5); 35.27, 35.49 (2×t, C-6); 65.92, 66.17 (2×d, C-4); 67.38 (t, CH$_2$-Z); 71.45 (t, CH$_2$Ph); 75.86 (d, C-3); 127.87, 127.98, 128.03, 128.57 (4×d, HC-Ph); 136.78, 137.73 (2×s, C-Ph); 155.15 (s, C=O-Z); 170.34 (s, C-1). m/z (CI NH$_3$): 91 (100%), 324 (M-CO$_2$+H$^-$, 60%), 385 (M+NH$_4^-$, 25%). (Found C, 68.56; H, 5.96; N, 3.51. C$_{21}$H$_{21}$NO$_5$ requires C, 68.68; H, 5.76; N, 3.81).

EXAMPLE 25

(2S,3R,4R) 3,4-Dihydroxypipecolic acid (4)

3-O-Benzyl-N-benzyloxycarbonyl-2,6-imino-2,5,6-trideoxy-D-lyxo-hexono-1,4-lactone (26) (321 mg, 0.875 mmol) was dissolved in a 2:1 mixture of acetic acid and water (10 ml) and stirred under hydrogen with palladium black (70 mg) for 48 hours. The reaction mixture was filtered through celite, the solvent removed and the product purified by flash chromatography (CMAW) and ion exchange chromatography. Freeze drying afforded (2S,3R,4R) 3,4-dihydroxypipecolic acid, monohydrate (140 mg, 89%) as a white crystalline solid, m.p. 253°–260° C. with decomposition, $[\alpha]_{20}^D$ −1.3° (c, 0.54 in water); $\nu_{max}$ (KBr disc) 3390, 1595 (CO), 1400, 1080, 1060 and 890 cm$^{-1}$; 1H NMR (D$_2$O) δ 1.48–1.61 (1H, m, 5-H); 1.99 (1H, ddt, H-5', J$_{5,5'}$ 14.4 Hz, J$_{5',6;5',6';5',4}$ 3.7 Hz); 2.88 (1H, ddd, 6-H, J$_{6,6'}$ 13.0 Hz, J$_{5,6}$ 11.9 Hz); 3.26 (1H, dt, H-6', J$_{5,6'}$ 3.7 Hz); 3.30 (1H, d, 2-H, J$_{2,3}$ 9.2 Hz); 3.52–3.61 (2H, m, H-3, H-4); 13C NMR (D$_2$O) δ 28.33 (t, C-2); 41.13 (t, C-1); 61.51 (d, H-5); 70.24, 71.85 (2×d, C-3,4); 172.43 (s, C-1). m/z: 124 (M-2×H$_2$O-H$^+$, 100%), 98 (M-H$_2$O-CO$_2$H$^+$, 95%), 116 (M-CO$_2$H$^+$, 75%), 162 (M+H$^+$, 67%). (Found C, 40.16; H, 7.10; N, 7.56. C$_6$H$_{11}$NO$_4$·H$_2$O requires C, 40.22; H, 7.31; N, 7.82).

Various other examples will be apparent to the person skilled in the art after reading the present disclosure without departing from the spirit and scope of the invention. It is intended that all such other examples be included within the scope of the appended claims.

What is claimed is:

1. A method for the synthesis of 1,4-dideoxy-1,4-imino-D-arabinitol (1) comprising carrying out the following stepwise reactions in solution phase and in about stoichiometric proportions of reactants in which compound numbers in parenthesis refer to compounds shown by chemical structure:

(a) esterifying 3-O-benzyl-1,2-O-isopropylidene-α-D-xylofuranose (8) at the primary hydroxyl with methansesulfonyl chloride to give the corresponding mesylate (9),

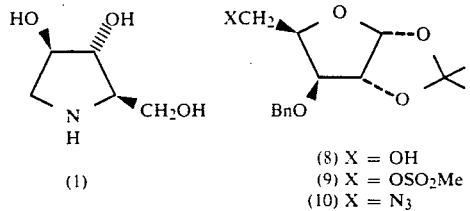

(8) X = OH
(9) X = OSO$_2$Me
(10) X = N$_3$ (b) reacting the mesylate (9) with azide ion-containing compound to introduce the azide function at C-5 and give a furanose (10), (c) converting the furanose (10) to the methyl furanosides (11) as a mixture of the α and β anomers by treatment with methanolic hydrogen chloride,

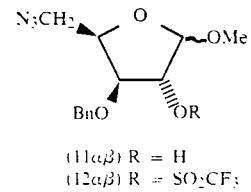

(11α,β) R = H
(12α,β) R = SO$_2$CF$_3$ (d) esterifying the methyl furanosides (11) at the free hydroxyl at C-2 with triflic anhydride to give the corresponding triflates (12), (e) catalytically hydrogenating the triflates (12) to reduce the azide to give the corresponding amine and provide ring closure to give the iminolyxofuranosides (13),

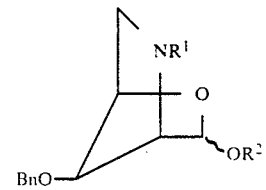

(13α,β) R$^1$ = H; R$^2$ = Me
(14α,β) R$^1$ = Z; R$^2$ = Me
(15α,β) R$^1$ = Z; R$^2$ = H (f) converting the iminolyxofuranosides (13) to the carbamates (14) by reaction with benzyl chloroformate, (g) subjecting the carbamates (14) to acid hydrolysis to give the lactol (15), (h) reducing the lactol (15) with sodium borohydride to give diol (16) from which the protecting groups are removed by hydrogenolysis to give the desired 1,4-dideoxy-1,4-imino-D-arabinitol (1)

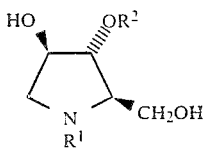

(16) R¹ = Z; R² = Bn
(1) R¹ = R² = H wherein Bn=CH₂Ph and Z=COOCH₂Ph.

2. A method for the synthesis of (2S,3R,4R)-3,4-dihydroxyproline (2) comprising carrying out the following stepwise reactions in solution phase and in about stoichiometric proportions of reactants in which compound numbers in parenthesis refer to compounds shown by chemical structure:

(a) esterifying 3-O-benzyl-1,2-O-isopropylidene-α-D-xylofuranose (8) at the primary hydroxyl with methanesulfonyl chloride to give the corresponding mesylate (9),

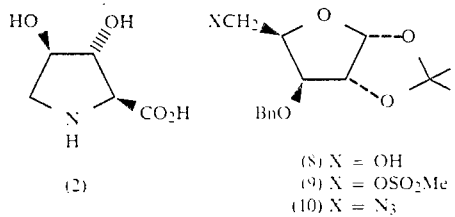

(2)

(8) X = OH
(9) X = OSO₂Me
(10) X = N₃

(b) reacting the mesylate (9) with azide ion-containing compound to introduce the azide function at C-5 and give a furanose (10), (c) converting the furanose (10) to the methyl furanosides (11) as a mixture of the α and β anomers by treatment with methanolic hydrogen chloride,

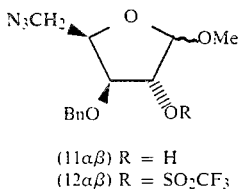

(11αβ) R = H
(12αβ) R = SO₂CF₃

(d) esterifying the methyl furanosides (11) at the free hydroxyl at C-2 with triflic anhydride to give the corresponding triflates (12), (e) catalytically hydrogenating the triflates (12) to reduce the azide to give the corresponding amine and provide ring closure to give the iminolyxofuranosides (13),

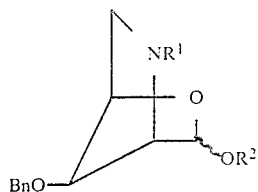

(13αβ) R¹ = H; R² = Me
(14αβ) R¹ = Z; R² = Me
(15αβ) R¹ = Z; R² = H (f) converting the iminolyxofuranosides (13) to the carbamates (14) by reaction with benzyl chloroformate, (g) subjecting the carbamates (14) to acid hydrolysis to give the lactol (15), (h) oxidizing the lactol (15) with bromine to give the benzyl-protected proline derivative (17) which is subjected to hydrogenolytic removal of the protecting groups to give the desired (2S,3R,4R)-3,4-dihydroxyproline (2)

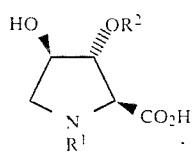

(17) R¹ = Z; R² = Bn
(2) R¹ = R² = H wherein Bn=CH₂Ph and Z=COOCH₂Ph.

3. A method for the synthesis of fagomine (3) comprising carrying out the following stepwise reactions in solution phase and in about stoichiometric proportions of reactants in which compound numbers in parenthesis refer to compounds shown by chemical structure:

(a) esterifying 3-O-benzyl-1,2-O-isopropylidene-α-D-lyxofuranose (8) at the free hydroxyl with triflic anhydride to give the triflate (18),

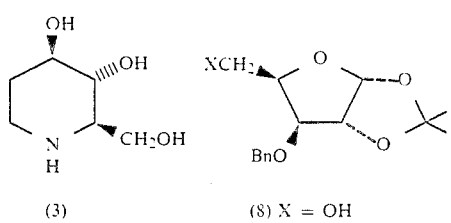

(3)    (8) X = OH (b) reacting the triflate (18) with alkali metal cyanide to give the nitrile (19),

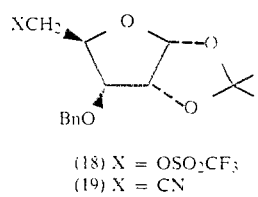

(18) X = OSO₂CF₃
(19) X = CN (c) converting the nitrile (19) to the methyl furanosides (20) as a mixture of their α and β anomers by treatment with methanolic hydrogen chloride,

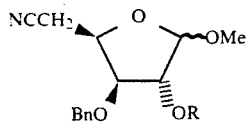

(20αβ) R = H
(21αβ) R = SO₂CF₃

(d) converting the methyl furanosides (20) to the triflates (21) by esterifying with triflic anhydride, (e) reducing the triflates (21) with borane-dimethyl sulfide to the corresponding 6-amino sugar followed by treatment with alkali metal carbonate to give the bicyclic amines (22),

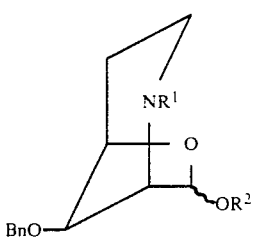

(22αβ) R¹ = H; R² = Me
(23αβ) R¹ = Z; R² = Me
(24αβ) R¹ = Z; R² = H (f) converting the bicyclic amines (22) to the carbamates (23) by reaction with benzyl chloroformate, (g) subjecting the carbamates (23) to hydrogenolysis to give the lactol (24), (h) reducing the lactol (24) with sodium borohydride to give a diol (25) from which the protecting groups are removed by hydrogenolysis to give the desired fagomine (3)

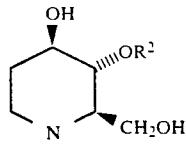

(25) R¹ = Z; R² = Bn
(3) R¹ = R² = H wherein Bn=CH₂Ph and Z=COOCH₂Ph.

4. A method for the synthesis of (2S, 3R, 4R)-3,4-dihydroxypipecolic acid (4) comprising carrying out the following stepwise reactions in solution phase and in about stoichiometric proportions of reactants in which cmpound numbers in parenthesis refer to compounds shown by chemical structure:

(a) esterifying 3-O-benzyl-1,2-O-isopropylidene-α-D-lyxofuranose (8) at the free hydroxyl with triflic anhydride to give the triflate (18),

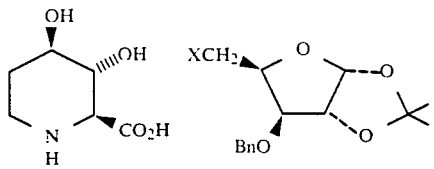

(4)   (8) X = OH (b) reacting the triflate (18) with alkali metal cyanide to give the nitrile (19),

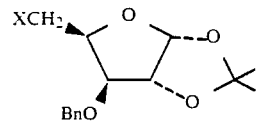

(18) X = OSO₂CF₃
(19) X = CN (c) converting the nitrile (19) to the methyl furanosides (20) as a mixture of their α and β anomers by treatment with methanolic hydrogen chloride,

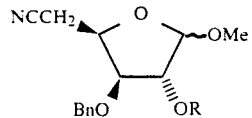

(20αβ) R = H
(21αβ) R = SO₂CF₃

(d) converting the methyl furanosides (20) to the triflates (21) by esterifying with triflic anhydride,
(e) reducing the triflates (21) with borane-dimethyl sulfide to the corresponding 6-amino sugar followed by treatment with alkali metal carbonate to give the bicyclic amines (22),

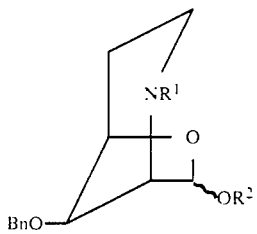

(22αβ) R¹ = H; R² = Me
(23αβ) R¹ = Z; R² = Me
(24αβ) R¹ = Z; R² = H (f) converting the bicyclic amines (22) to the carbamates (23) by reaction with benzyl chloroformate,
(g) subjecting the carbamates (23) to hydrogenolysis to give the lactol (24),
(h) oxidizing the lactol (24) with bromine to give the benzyl-protected pipecolic derivative (26) which is subjected to hydrogenolytic removal of the protecting groups to give the desired (2S,3R,4R)-3,4-dihydroxypipecolic acid (4)

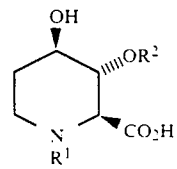

(26) R¹ = Z; R² = Bn
(4) R¹ = R² = H wherein Bn=CH₂Ph and Z=COOCH₂Ph.

* * * * *